United States Patent
Shelton, IV et al.

(10) Patent No.: US 11,026,681 B2
(45) Date of Patent: Jun. 8, 2021

(54) SURGICAL INSTRUMENT WITH RECESSED CONTACTS AND ELECTRICALLY INSULATING BARRIERS

(71) Applicant: ETHICON LLC, Guaynabo, PR (US)

(72) Inventors: Frederick E. Shelton, IV, Hillsboro, OH (US); Jerome R. Morgan, Cincinnati, OH (US); John E. Brady, Liberty Township, OH (US); Austin E. Wise, Cincinnati, OH (US); Gregory J. Bakos, Mason, OH (US)

(73) Assignee: Cilag GmbH International, Zug (CH)

( * ) Notice: Subject to any disclaimer, the term of this patent is extended or adjusted under 35 U.S.C. 154(b) by 372 days.

(21) Appl. No.: 15/934,160

(22) Filed: Mar. 23, 2018

(65) Prior Publication Data

US 2019/0290269 A1    Sep. 26, 2019

(51) Int. Cl.
*A61B 17/072* (2006.01)
*A61B 18/14* (2006.01)
(Continued)

(52) U.S. Cl.
CPC ........ *A61B 17/072* (2013.01); *A61B 18/1445* (2013.01); *A61B 17/00234* (2013.01);
(Continued)

(58) Field of Classification Search
CPC .. H01R 4/26; H01R 13/5224; H01R 13/5219; H01R 2201/12; H01R 4/56; A61B 2017/07271; A61B 2017/00017
See application file for complete search history.

(56) References Cited

U.S. PATENT DOCUMENTS 5,400,267 A * 3/1995 Denen .................... A61B 17/00
128/908
5,792,135 A   8/1998 Madhani et al.
(Continued)

FOREIGN PATENT DOCUMENTS

EP           2 839 797 A2    2/2015
WO     WO 2015/153642 A1   10/2015

OTHER PUBLICATIONS

Hollister, S., "Waterproofing explained: How Apple, Samsung and Sony keep the liquid out," cnet.com, Sep. 21, 2016, downloaded from https://www.cnet.com/news/how-does-waterproofing-work-apple-iphone-7-samsung-galaxy-s7-sony-xperia/, copyrighted by CBS Interactive Inc., 8 pgs.

(Continued)

*Primary Examiner* — Andrew M Tecco
*Assistant Examiner* — Nicholas E Igbokwe
(74) *Attorney, Agent, or Firm* — Frost Brown Todd LLC

(57) ABSTRACT

A surgical instrument includes a body assembly, a shaft assembly configured to releasably attach to and extend distally from the body assembly, and an end effector at a distal end of the shaft assembly. A first electrical connector is coupled to one of the body assembly or the shaft assembly and includes a first connector body and a first electrical contact recessed within the first connector body. A second electrical connector is coupled to the other of the body assembly or the shaft assembly and includes a second connector body and a second electrical contact supported by the second connector body. The first connector body is configured to receive the second electrical contact therein to enable the electrical contacts to electrically couple together when the shaft assembly is attached to the body assembly.

20 Claims, 20 Drawing Sheets

(51) Int. Cl.
*A61B 17/29* (2006.01)
*A61B 17/00* (2006.01)

(52) U.S. Cl.
CPC ..... *A61B 17/29* (2013.01); *A61B 2017/07257* (2013.01); *A61B 2017/07271* (2013.01); *A61B 2017/2901* (2013.01); *A61B 2017/2926* (2013.01); *A61B 2017/2946* (2013.01); *A61B 2017/2948* (2013.01)

(56) References Cited

U.S. PATENT DOCUMENTS

| | | | |
|---|---|---|---|
| 5,817,084 A | 10/1998 | Jensen | |
| 5,817,093 A | 10/1998 | Williamson, IV et al. | |
| 5,878,193 A | 3/1999 | Wang et al. | |
| 6,231,565 B1 | 5/2001 | Tovey et al. | |
| 6,287,136 B1* | 9/2001 | Deutsch | H01R 13/213 439/144 |
| 6,364,888 B1 | 4/2002 | Niemeyer et al. | |
| 6,783,524 B2 | 8/2004 | Anderson et al. | |
| 7,404,508 B2 | 7/2008 | Smith et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 7,997,917 B1* | 8/2011 | O'Neill | H01R 13/5208 439/275 |
| 8,408,439 B2 | 4/2013 | Huang et al. | |
| 8,453,914 B2 | 6/2013 | Laurent et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,608,045 B2 | 12/2013 | Smith et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,991,678 B2 | 3/2015 | Wellman et al. | |
| 9,072,535 B2 | 7/2015 | Shelton, IV et al. | |
| 9,186,142 B2 | 11/2015 | Fanelli et al. | |
| 9,301,759 B2 | 4/2016 | Spivey et al. | |
| 9,345,481 B2 | 5/2016 | Hall et al. | |
| 9,724,094 B2 | 8/2017 | Baber et al. | |
| 9,795,379 B2 | 10/2017 | Leimbach et al. | |
| 9,839,425 B2 | 12/2017 | Zergiebel et al. | |
| 9,913,642 B2 | 3/2018 | Leimbach et al. | |
| 2011/0121049 A1* | 5/2011 | Malinouskas | A61B 90/92 227/175.1 |
| 2011/0125138 A1* | 5/2011 | Malinouskas | A61B 90/98 606/1 |
| 2012/0078278 A1* | 3/2012 | Bales, Jr. | A61B 17/320092 606/169 |
| 2014/0012289 A1* | 1/2014 | Snow | A61B 17/068 606/130 |
| 2014/0263541 A1 | 9/2014 | Leimbach et al. | |
| 2014/0263552 A1 | 9/2014 | Hall et al. | |
| 2015/0272579 A1* | 10/2015 | Leimbach | A61L 2/087 227/178.1 |
| 2015/0272580 A1* | 10/2015 | Leimbach | H01R 39/10 227/175.1 |
| 2016/0066911 A1 | 3/2016 | Baber et al. | |
| 2016/0310134 A1 | 10/2016 | Contini et al. | |

OTHER PUBLICATIONS

U.S. Appl. No. 15/635,663, filed Jun. 28, 2017.
U.S. Appl. No. 15/635,631, filed Jun. 28, 2017.
U.S. Appl. No. 15/635,837, filed Jun. 28, 2017.
U.S. Appl. No. 15/636,096, filed Jun. 28, 2017.
U.S. Appl. No. 15/934,139, filed Mar. 23, 2018.
U.S. Appl. No. 15/934,148, filed Mar. 23, 2018.
U.S. Appl. No. 15/934,166, filed Mar. 23, 2018.
U.S. Appl. No. 15/934,173, filed Mar. 23, 2018.
U.S. Appl. No. 15/934,180, filed Mar. 23, 2018.
U.S. Appl. No. 15/934,190, filed Mar. 23, 2018.

* cited by examiner

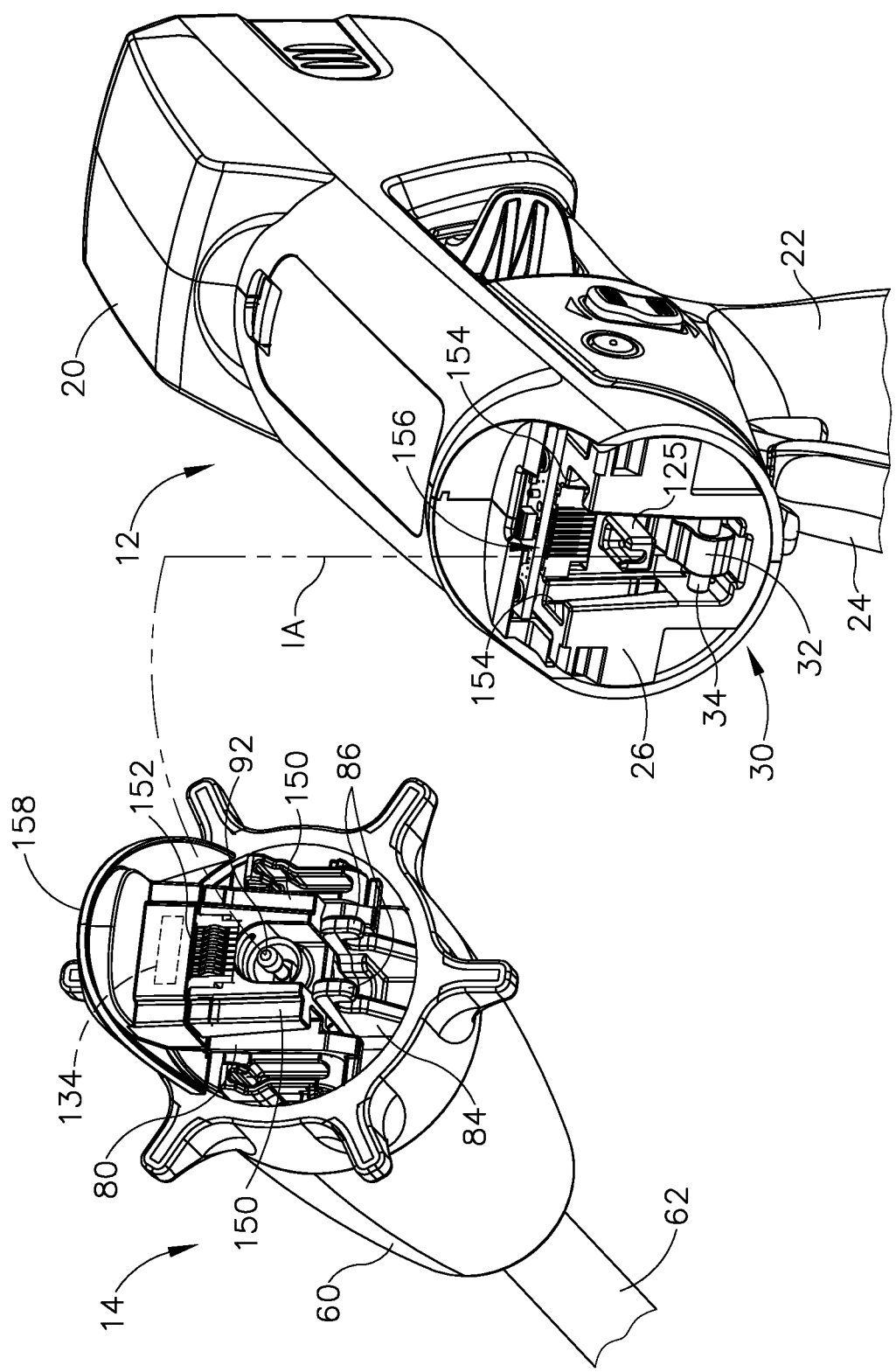

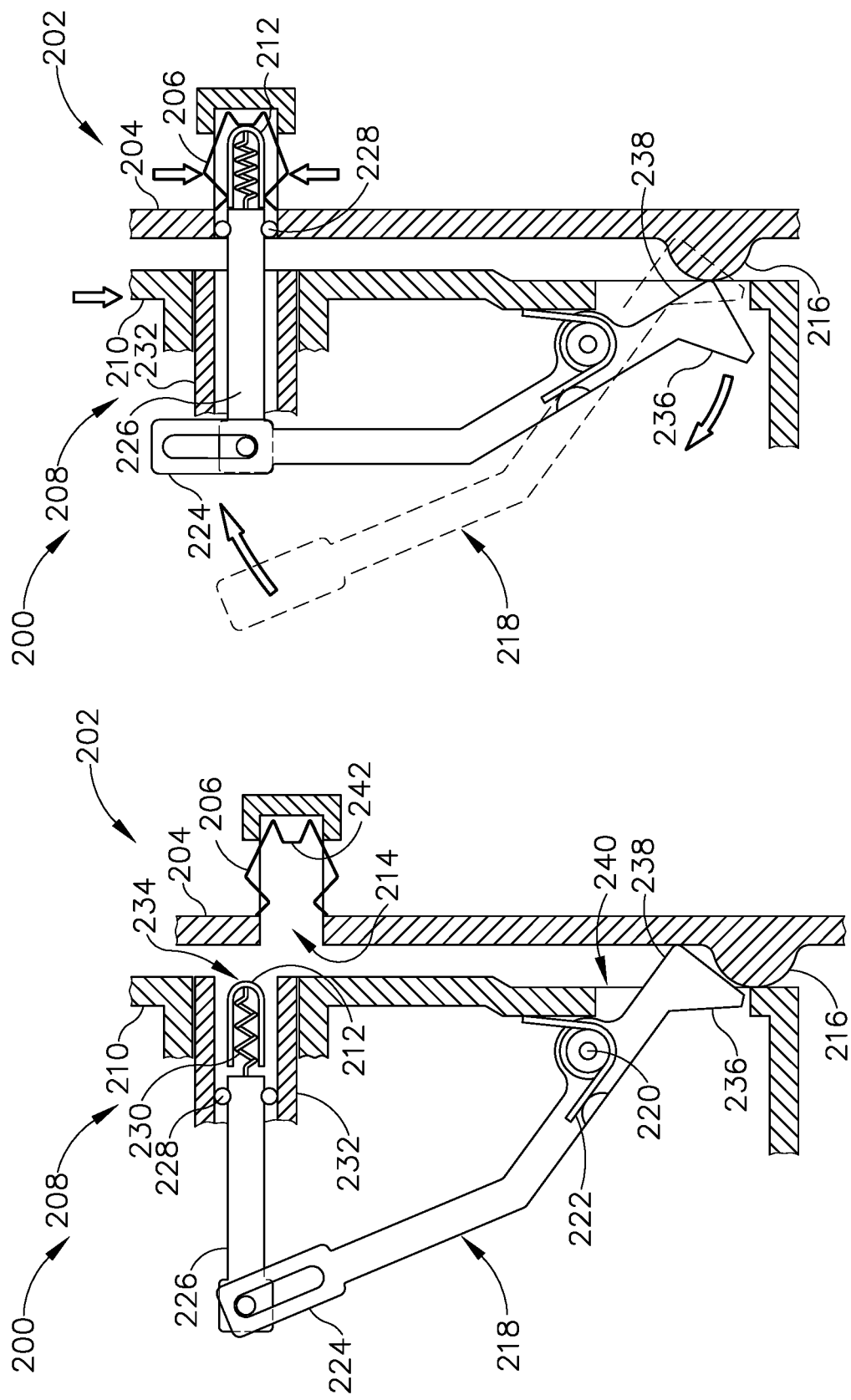

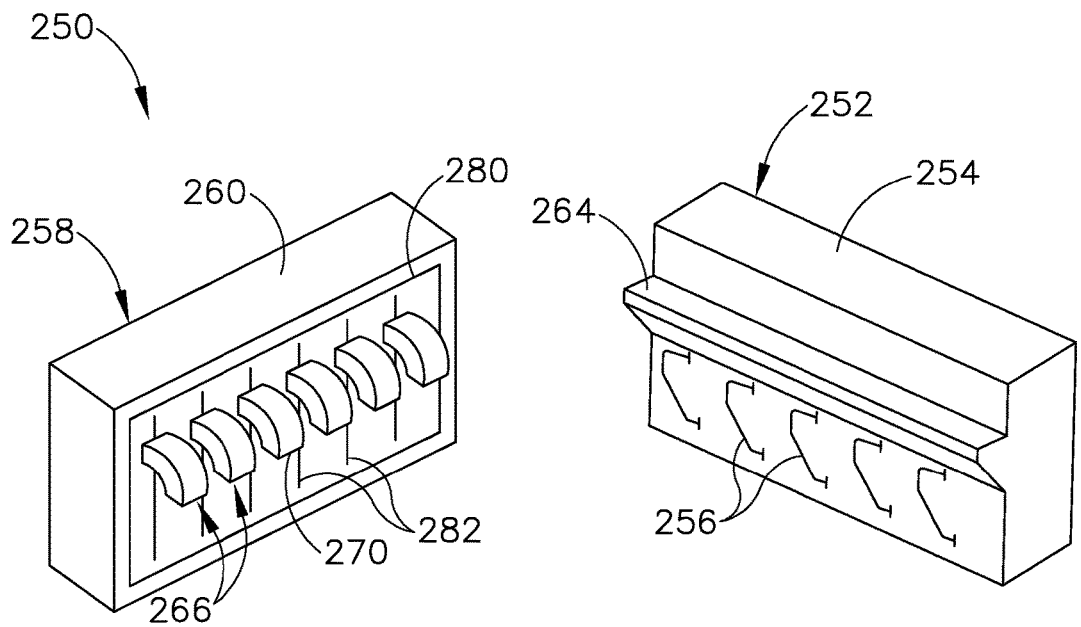
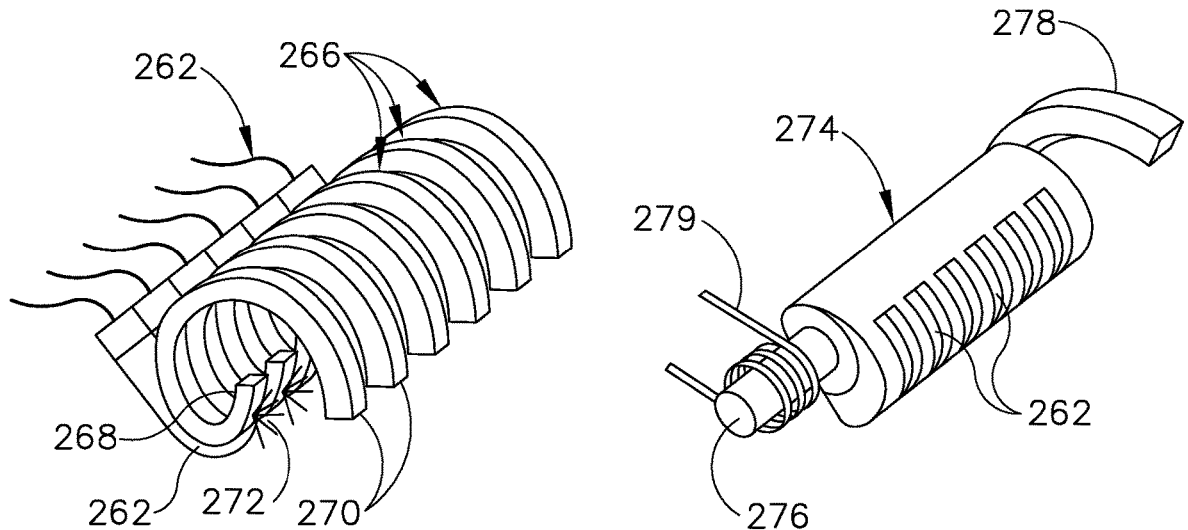
Fig.13
Fig.14  Fig.15

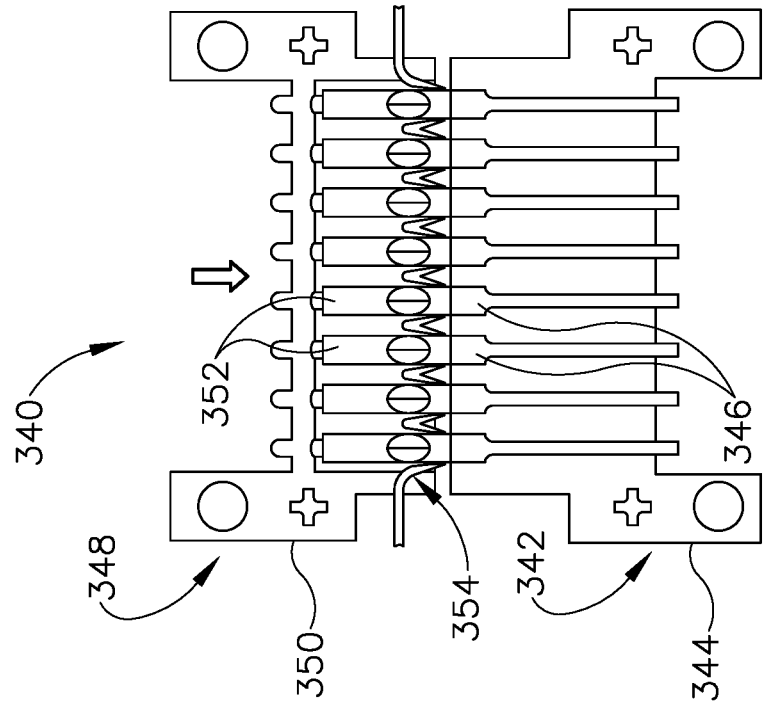
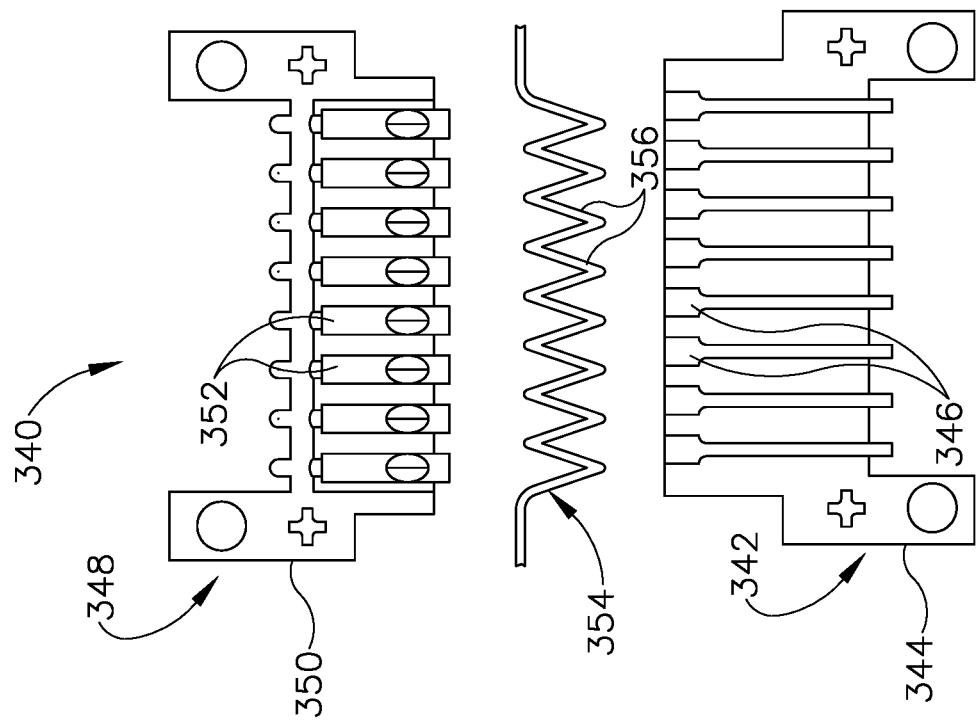

SURGICAL INSTRUMENT WITH RECESSED CONTACTS AND ELECTRICALLY INSULATING BARRIERS

BACKGROUND

Endoscopic surgical instruments may be preferred over traditional open surgical devices in certain instances to create a smaller surgical incision in the patient and thereby reduce the post-operative recovery time and complications. Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 7,404,508, entitled "Surgical Stapling and Cutting Device," issued Jul. 29, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued Nov. 17, 2015; and U.S. Pat. No. 9,795,379, entitled "Surgical Instrument with Multi-Diameter Shaft," issued Oct. 24, 2017. The disclosure of each of the above-cited U.S. patents is incorporated by reference herein.

While the surgical staplers referred to above are described as being used in endoscopic procedures, such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Of course, surgical staplers may be used in various other settings and procedures.

While several surgical instruments and systems have been made and used, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4 depicts another perspective view of the surgical instrument of FIG. 1 in a separated state, showing additional details of a distal end of the handle assembly and a mating proximal end of the interchangeable shaft assembly;

FIG. 10A depicts a schematic side cross-sectional view of the electrical connection assembly of FIG. 9, showing the first and second connectors in a confronting but disengaged state;

FIG. 10B depicts a schematic side cross-sectional view of the electrical connection assembly of FIG. 10A, showing the first and second connectors in an engaged state.

FIG. 13 depicts a schematic perspective view of another exemplary electrical connection assembly suitable for use with the surgical instrument of FIG. 1, showing first and second connectors of the connection assembly in a disengaged state;

FIG. 14 depicts a perspective view of a plurality of rotating elements and corresponding electrical contacts of the second connector of FIG. 13;

FIG. 15 depicts a perspective view an exemplary alternative rotating structure and corresponding electrical contacts suitable for use with the second connector of FIG. 13;

FIG. 20A depicts an end view of another exemplary electrical connection assembly suitable for use with the surgical instrument of FIG. 1, showing first and second connectors of the connection assembly in a disengaged state;

FIG. 20B depicts an end view of the electrical connection assembly of FIG. 20A, showing the first and second connectors in an engaged state;

Figure 1:
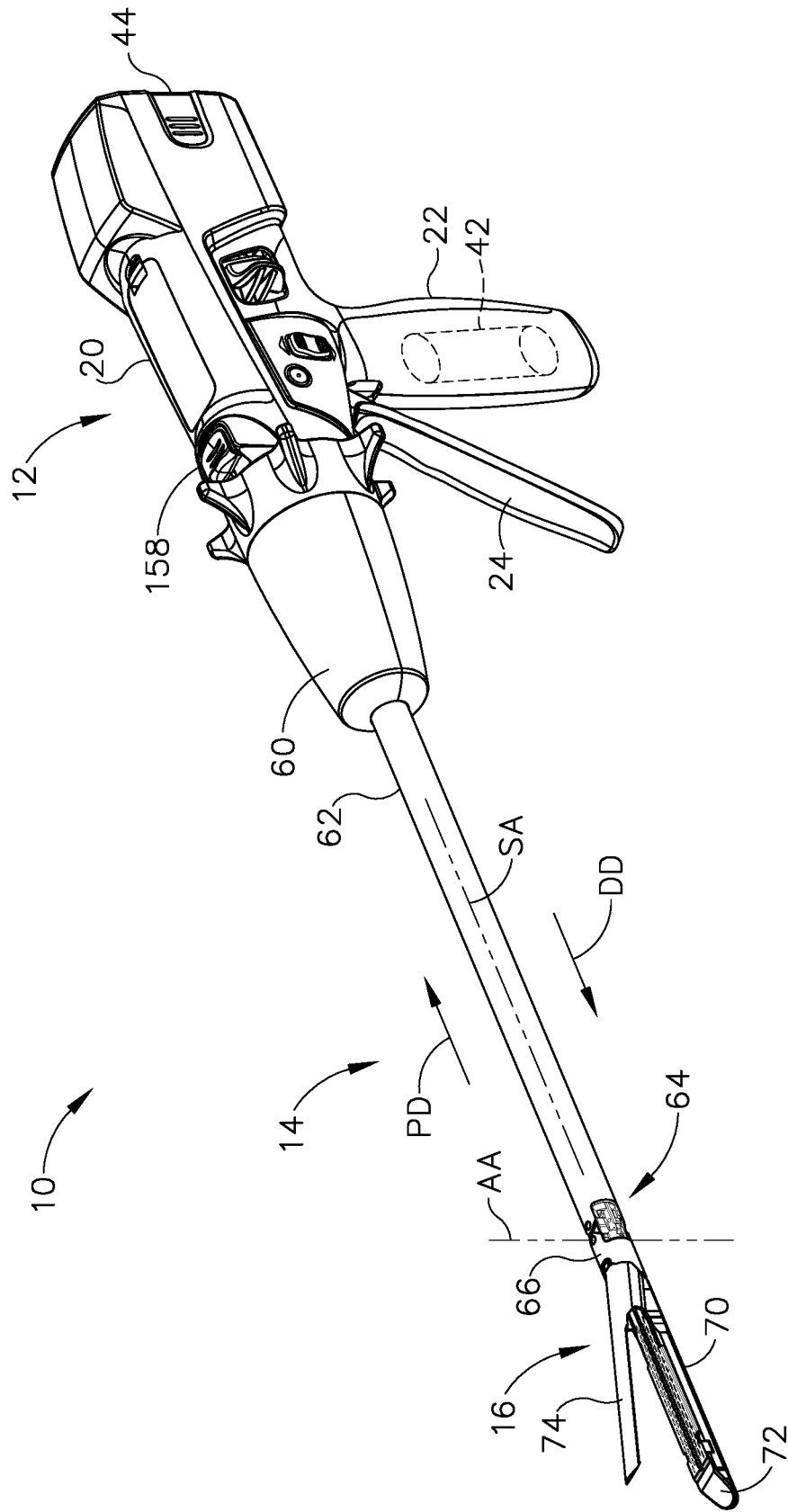
FIG. 1 depicts a perspective view of an exemplary surgical instrument having a handle assembly and an interchangeable shaft assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, clinician, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. Exemplary Surgical Stapling Instrument

Figure 2:
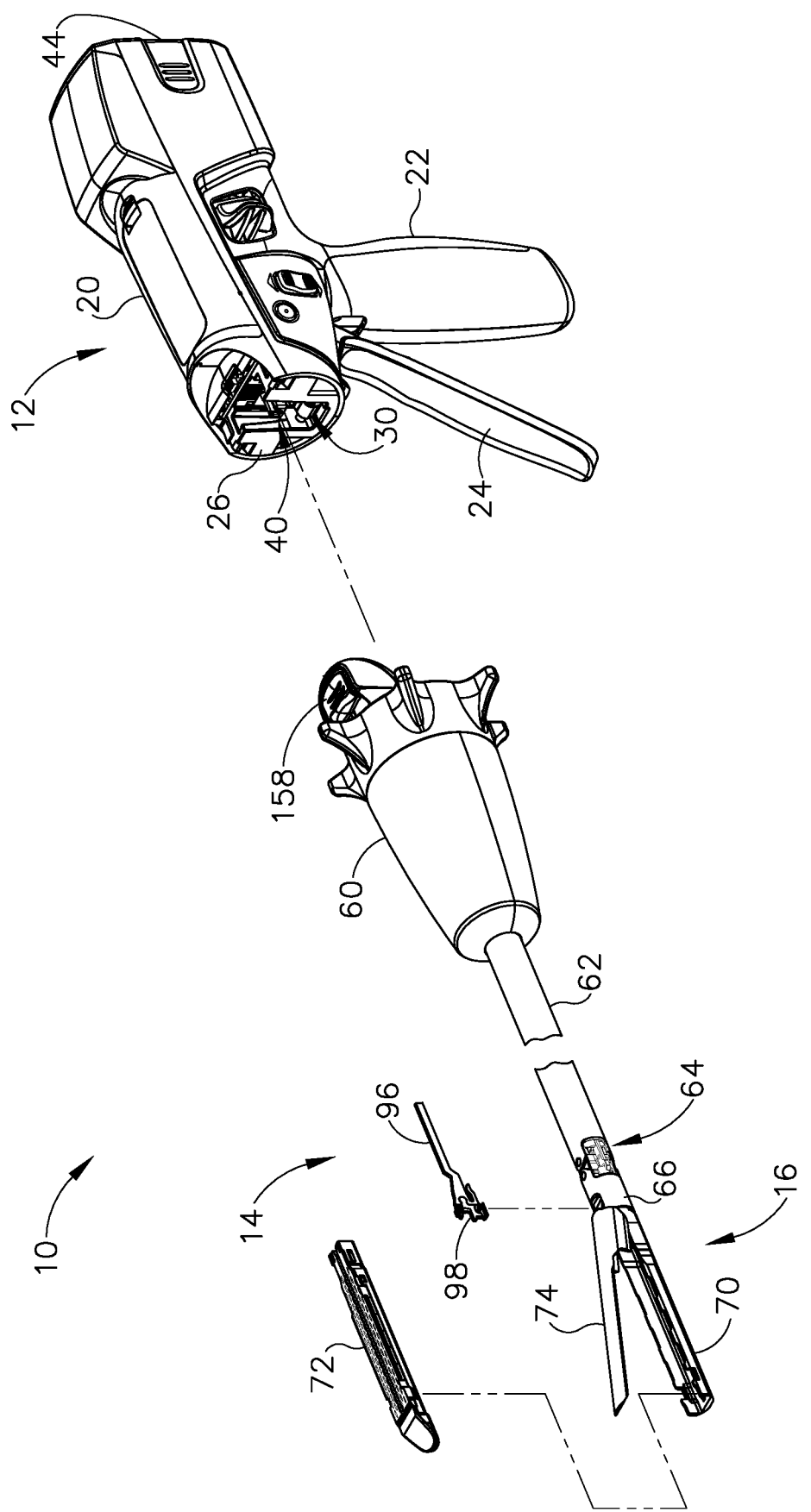
FIG. 2 depicts a partially exploded perspective view of the surgical instrument of FIG. 1, showing the interchangeable shaft assembly separated from the handle assembly.

FIGS. 1-2 show a motor-driven surgical instrument (10) suitable for use in a variety of surgical procedures. In the illustrated example, instrument (10) includes a handle assembly (12) and an interchangeable shaft assembly (14) releasably coupled to and extending distally from handle assembly (12). Interchangeable shaft assembly (14) includes a surgical end effector (16) arranged at a distal end thereof, and which is configured to perform one or more surgical tasks or procedures. In some applications, interchangeable shaft assembly (14) may be effectively employed with a tool drive assembly of a robotically controlled or automated surgical system. For example, interchangeable shaft assembly (14) may be employed with various robotic systems, instruments, components, and methods such as those disclosed in U.S. Pat. No. 9,072,535, entitled "Surgical Stapling Instruments With Rotatable Staple Deployment Arrangements," issued Jul. 7, 2015, the disclosure of which is incorporated by reference herein.

A. Handle Assembly of Surgical Stapling Instrument

Handle assembly (12) comprises a body (20) that includes a pistol grip (22) configured to be grasped by a clinician, and a closure trigger (24) configured to pivot toward and away from pistol grip (22) to selectively close and open end effector (16), as described in greater detail below. In the present example, end effector (16) is configured to cut and staple tissue captured by end effector (16). In other examples, end effector (16) may be configured to treat tissue via application of various other types of movements and energies, such as radio frequency (RF) energy and/or ultrasonic energy, for example.

Figure 3A:
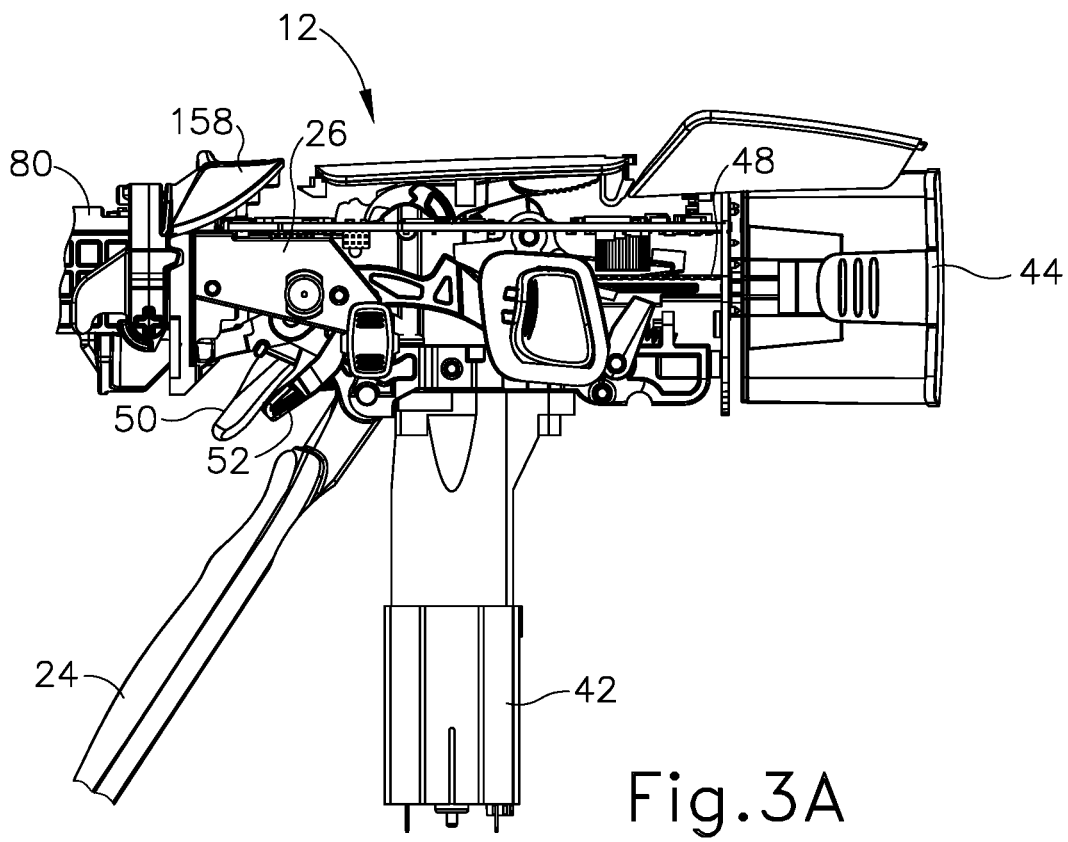
FIG. 3A depicts a side elevational view of the surgical instrument of FIG. 1, with a body of the handle assembly omitted, showing a closure trigger of the handle assembly in an unactuated position.
Figure 3B:
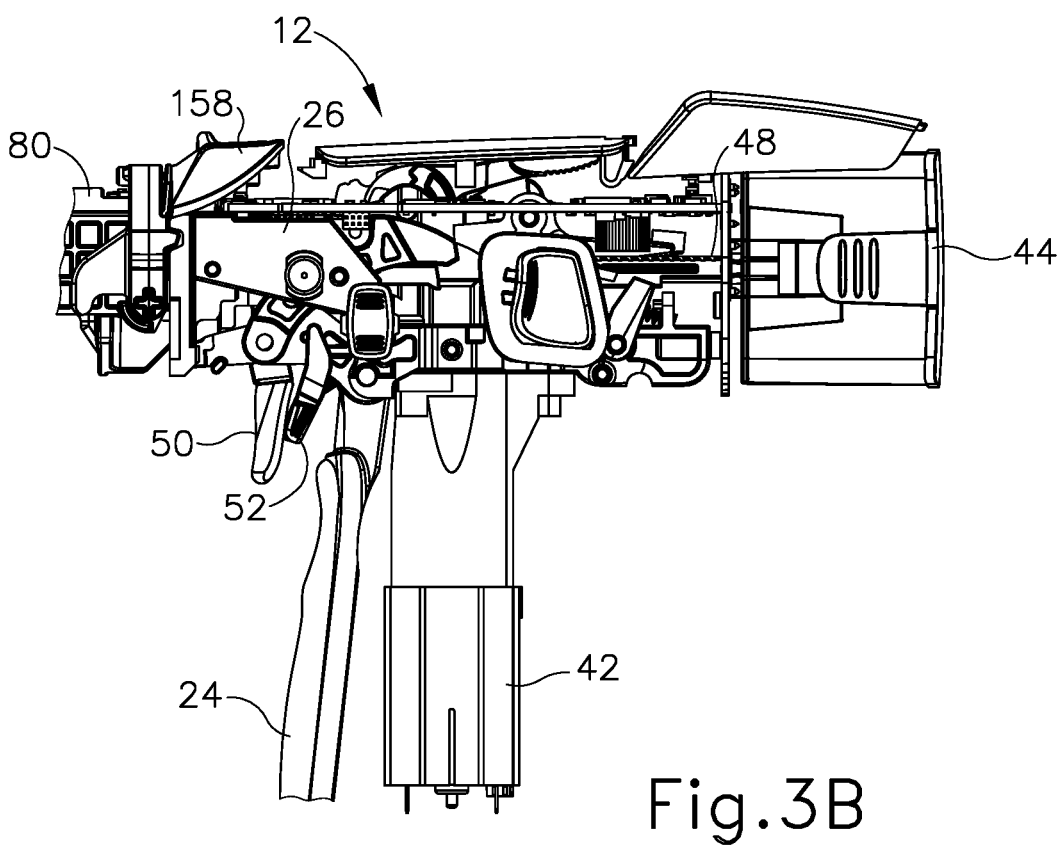
FIG. 3B depicts a side elevational view of the surgical instrument of FIG. 1, with a body of the handle assembly omitted, showing a closure trigger of the handle assembly in an actuated position.

As seen in FIGS. 2-4, handle assembly body (20) houses a support structure in the form of a handle frame (26) that supports a plurality of drive systems configured to generate and apply various control motions to corresponding portions of interchangeable shaft assembly (14). In particular, handle frame (26) supports a first drive system in the form of a closure drive system (30) that is operable to selectively close and open end effector (16) to thereby capture and release tissue. Closure drive system (30) includes an actuator in the form of closure trigger (24), which is pivotally supported by handle frame (26) and is operatively coupled with end effector (16) via components of shaft assembly (14) described below. Closure trigger (24) is configured to be squeezed by a clinician toward pistol grip (22) from an unactuated position (FIG. 3A) that provides end effector (16) in an open state for releasing tissue, to an actuated position (FIG. 3B) that provides end effector (16) in a closed state for clamping tissue. Closure trigger (24) may be biased toward the unactuated position by a resilient member (not shown). As seen best in FIG. 4, closure drive system (30) further comprises a linkage assembly that couples closure trigger (24) with end effector (16). The linkage assembly includes a closure link (32) and a transversely extending attachment pin (34) coupled to a distal end of closure link (32). Attachment pin (34) and the distal end of closure link (32) are accessible through a distal opening in handle assembly (12).

Handle assembly body (20) further supports a second drive system in the form of a firing drive system (40) configured to apply firing motions to corresponding portions of interchangeable shaft assembly (14) and its end effector (16). In the present example, firing drive system (40) employs an electric motor (42) that is housed within pistol grip (22) of handle assembly (12) and is operatively coupled with end effector (16), as described below. Electric motor (42) may be of any suitable type, such as a DC brushed motor, a brushless motor, a cordless motor, a synchronous motor, a stepper motor, or any other suitable type of electric motor. Electric motor (42) is powered by a power source shown in the form of a power pack (44) removably coupled to a proximal portion of handle assembly body (20). Power pack (44) includes one or more batteries (not shown) of any suitable type, and may be rechargeable or replaceable.

As seen in FIG. 4, electric motor (42) is electrically coupled to and controlled by a circuit board (46) supported by handle frame (26) within handle assembly body (20). Circuit board (46) may include a microcontroller and is configured to direct power from power pack (44) to electric motor (42) and thereby energize motor (42) to fire end effector (16). Electric motor (42) is configured to interface with a drive gear arrangement (not shown) that is operable to actuate an elongate drive member (48) axially relative to handle frame (26) in response to activation of motor (42). As seen best in FIG. 5, a distal end of drive member (48) is exposed through a distal opening of handle assembly (12) and is configured to couple to a translating member of shaft assembly (14) to thereby operatively couple motor (42) with end effector (16), as described below.

Electric motor (42) is energized by battery pack (44) in response to actuation of a firing trigger (50), which is pivotally supported by handle assembly (12) as best seen in FIGS. 3A and 3B. In the present example, firing trigger (50) is positioned "outboard" of closure trigger (24). Similar to closure trigger (24), firing trigger (50) is configured to be squeezed by the clinician toward pistol grip (22) from an unactuated position (FIG. 3B) to an actuated position (not shown). Firing trigger (50) may be biased toward the unactuated position by a resilient member (not shown). When firing trigger (50) is depressed from the unactuated position to the actuated position, firing trigger (50) causes battery pack (44) to energize motor (42) to actuate drive member (48) longitudinally and thereby fire end effector (16). As shown in FIGS. 3A and 3B, handle assembly (12) further includes a firing trigger safety button (52) that is selectively pivotable between a safety position and a firing position to prevent inadvertent actuation of firing trigger (50).

Figure 5:
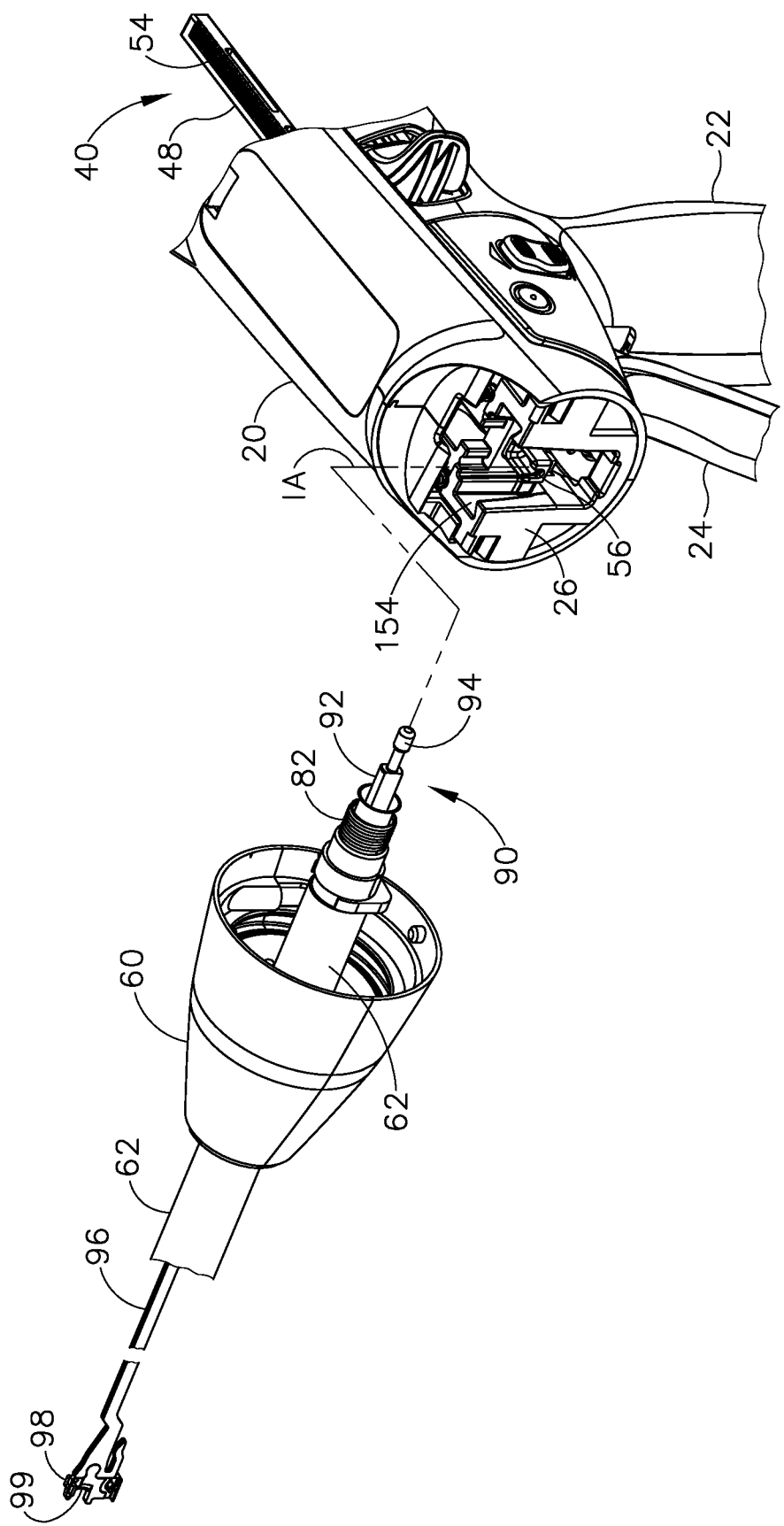
FIG. 5 depicts another perspective view of the surgical instrument of FIG. 1 in a separated state, with certain components of the handle assembly and the shaft assembly omitted to reveal components of a firing system.

As shown best in FIG. 5, elongate drive member (48) of firing drive system (40) includes a rack of teeth (54) formed on at least a proximal portion thereof for meshing engagement with a corresponding drive gear arrangement (not shown) that interfaces with electric motor (42). Drive member (48) further includes an attachment cradle (56) on a distal end thereof, which is configured to receive and couple with an elongate translating member of shaft assembly (14), described below. Drive member (48) is configured to configured to be driven by motor (42) from a proximal position to a distal position to thereby actuate the translating member of shaft assembly (14) and fire end effector (16).

B. Interchangeable Shaft Assembly of Surgical Stapling Instrument

As shown in FIGS. 1-2, interchangeable shaft assembly (14) of the present example includes a proximal nozzle (60), an elongate proximal closure tube (62) extending distally from nozzle (60), an articulation joint (64) disposed at a distal end of the closure tube (62), a distal closure tube segment (66) coupled to a distal end of articulation joint (64), and end effector (16) extending distally therefrom.

End effector (16) includes a first jaw comprising an elongate channel (70) that receives a cartridge (72), and a second jaw comprising an anvil (74) configured to pivot relative to channel (70) between open and closed positions for clamping tissue between anvil (74) and cartridge (72). Cartridge (72) is shown in the form of a conventional staple cartridge having features described in greater detail below, and is configured to fire a plurality of staples into tissue clamped by end effector (16). In other examples, end effector (16) may be suitably configured to apply a variety of other types of motions and energies to tissue captured by end effector (16), such as radio frequency (RF) energy and/or ultrasonic energy, for example. For instance, cartridge (72) may be configured to apply RF to tissue as generally disclosed in U.S. Ser. No. 15/636,096, entitled "Surgical System Couplable With Staple Cartridge And Radio Frequency Cartridge, And Method Of Using Same," filed Jun. 28, 2017, the disclosure of which is incorporated by reference herein.

Anvil (74) of end effector (16) is operatively coupled with closure drive system (30) of handle assembly (12), and is configured to pivot between open and closed positions, about a pivot axis that extends transversely to shaft axis (SA), in response to actuation of closure trigger (24). In particular, anvil (74) is configured to as assume an open position when closure trigger (24) is in the unactuated position, and a closed position when closure trigger (24) depressed to the actuated position. Anvil (74) is coupled with closure drive system (30) via proximal closure tube (62) and distal closure tube segment (66), among other components described below. Proximal closure tube (62) and distal closure tube segment (66) are configured to translate proximally and distally relative to nozzle (60) to thereby actuate anvil (74) about its pivot axis in response to actuation of closure trigger (24).

Articulation joint (64) is configured to provide articulation of end effector (16) relative to proximal closure tube (62) and corresponding components of shaft assembly (14) about an articulation axis (AA) that extends transversely to shaft axis (SA). In some examples, end effector (16) may be articulated to a desired orientation by pushing end effector (16) against soft tissue and/or bone within the patient. In other examples, end effector (16) may be articulated by an articulation driver (not shown).

As best seen in FIG. 4, nozzle (60) of interchangeable shaft assembly (14) houses a support structure in the form of a tool chassis (80) that rotatably supports nozzle (60). Nozzle (60) and end effector (16) are configured to rotate relative to tool chassis (80) about shaft axis (SA), as indicated in FIG. 1. As shown in FIG. 5, proximal closure tube (62) houses an internal spine (82) that is rotatably supported by tool chassis (80) (omitted from view in FIG. 5) at a proximal end and is coupled to end effector (16) at a distal end. Tool chassis (80) further supports a closure shuttle (84) that is configured to translate proximally and distally relative to tool chassis (80). A distal end of closure shuttle (84) is coupled to and rotatably supports a proximal end of proximal closure tube (62). A proximal end of closure shuttle (84) includes a pair of proximally extending hooks (86) configured to couple with closure drive system (30) of handle assembly (12). In particular, hooks (86) are configured to releasably capture attachment pin (34) of closure drive system (30) when interchangeable shaft assembly (14) is coupled with handle assembly (12). Accordingly, actuation of closure trigger (24) to the actuated position (see FIG. 3B) drives closure shuttle (84) distally, which in turn drives proximal closure tube (62) and distal closure tube segment (66) distally, thereby actuating anvil (74) to a closed position for clamping tissue with end effector (16). Returning trigger to the unactuated position (see FIG. 3A) actuates these components proximally, thereby returning anvil (74) to an open position.

As seen best in FIG. 5, interchangeable shaft assembly (14) further includes an internal firing system (90) configured to operatively couple with firing drive system (40) of handle assembly (12) when shaft assembly (14) is coupled to handle assembly (12). Firing system (90) includes an intermediate firing shaft (92) slidably received within spine (82) and proximal closure tube (62). Intermediate firing shaft (92) includes a proximal end having an attachment lug (94) configured to rotatably seat within attachment cradle (56) of drive member (48) of firing drive system (40), and a distal end configured to couple to an elongate knife bar (96). Knife bar (96) is connected at its distal end to a knife member (98), which includes a sharpened cutting edge (99) configured to sever tissue clamped by end effector (16) as knife member advances distally through staple cartridge (72). Accordingly, actuation of firing trigger (50) actuates drive member (48) distally, which in turn drives intermediate firing shaft (92), knife bar (96), and knife member (98) distally to thereby cut tissue and simultaneously fire staple cartridge (72), as described below. Knife member (98) may include one or more anvil engagement features configured to engage and maintain anvil (74) in a closed state throughout cutting and stapling of tissue.

Figure 6:
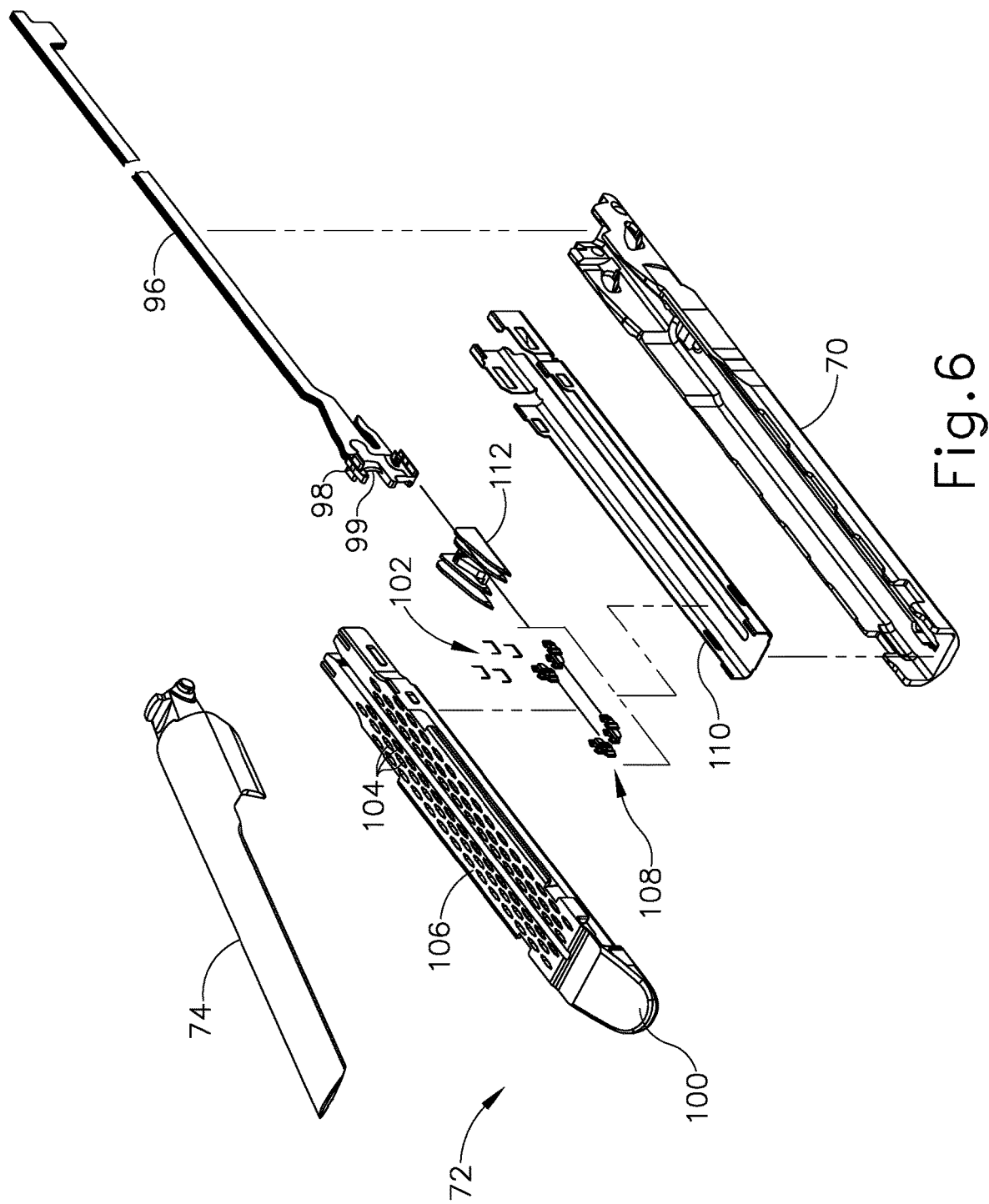
FIG. 6 depicts an exploded perspective view of an end effector of the surgical instrument of FIG. 1, in combination with certain components of the firing system.

As seen best in FIG. 6, staple cartridge (72) includes a molded cartridge body (100) that houses a plurality of staples (102) within staple cavities (104) that open upwardly through a staple deck (106) of cartridge body (100). A plurality of staple drivers (108) are positioned within staple cavities (104), beneath staples (102). A cartridge tray (110) covers an open bottom side of cartridge body (100) and holds together the various components of staple cartridge (72). A wedge sled (112) is slidably received within slots formed in cartridge body (100), and is driven distally by knife member (98) upon actuation of firing drive system (40). As wedge sled (112) advances distally through staple cartridge (72), wedge sled (112) cams staple drivers (108) upwardly to thereby drive staples (102) through tissue clamped by anvil (74) and into staple forming pockets (not shown) formed in anvil (74), thereby deforming staples (102). Simultaneously, cutting edge (99) of knife member (98) severs the tissue clamped in end effector (16). After firing staple cartridge (72), knife member (98) may be retracted to a proximal position to thereby permit opening of anvil (74) and release of the stapled/severed tissue.

C. Electrical Connections within Surgical Instrument

Interchangeable shaft assembly (14) and variations thereof that are suitable for use with handle assembly (12) may employ one or more sensors and/or various other electrical components that require electrical communication with handle circuit board (46) of handle assembly (12). For instance, a proximal portion of shaft assembly (14) and/or end effector (16) may include one or more sensors (see e.g., FIG. 8) and/or one or more RF electrodes (not shown) configured to electrically couple with handle circuit board (46) to enable operation thereof. As described below, shaft assembly (14) is suitably configured to enable rotation of end effector (16), among other components of shaft assembly (14), relative to handle assembly (12) while maintaining electrical coupling between shaft assembly (14) and handle assembly (12).

Figure 7:
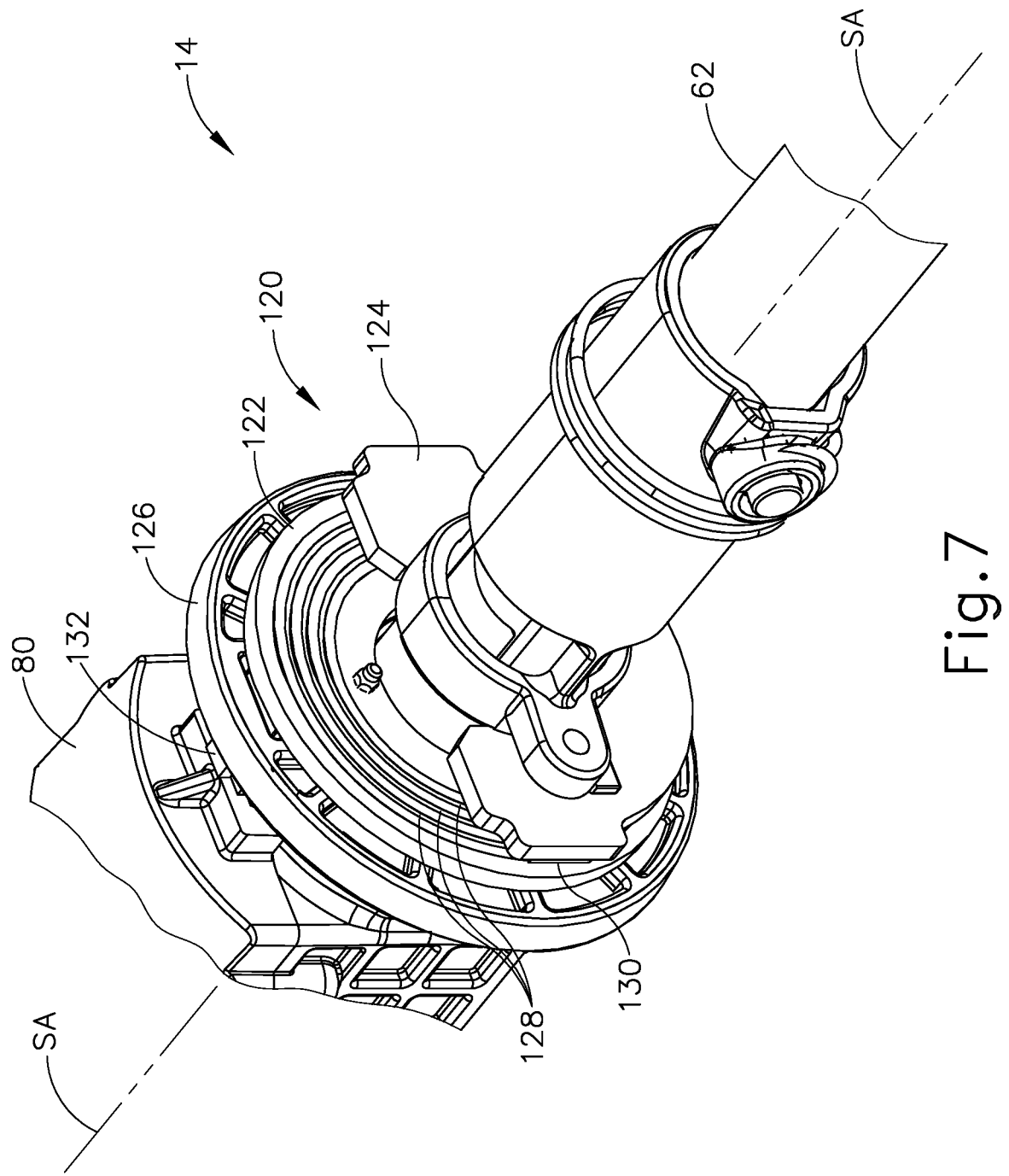
FIG. 7 depicts a perspective view of a proximal portion of the interchangeable shaft assembly of the surgical instrument of FIG. 1, with a nozzle of the shaft assembly omitted to reveal details of an internal slip ring assembly.

As shown in FIG. 7, interchangeable shaft assembly (14) includes a slip ring assembly (120) housed within nozzle (60). Slip ring assembly (120) is configured to electrically couple shaft assembly (14) with handle assembly (12) for communication of electrical power and/or sensor signals between end effector (16) and handle circuit board (46). Slip ring assembly (120) is configured to provide such electrical communication while facilitating rotation of nozzle (60) and end effector (16), among other rotating components of shaft assembly (14), relative to tool chassis (80) and handle assembly (12) about shaft axis (SA). Slip ring assembly (120) comprises a proximal connector flange (122) mounted to a chassis flange (126) that extends distally from tool chassis (80), and a distal connector flange (124) secured to an interior of nozzle (60). Distal connector flange (124) is configured to rotate with nozzle (60) relative to tool chassis (80) and chassis flange (126). Accordingly, the proximal face of distal connector flange (124) confronts and is configured to rotate relative to a distal face of proximal connector flange (122), about shaft axis (SA).

The distal face of proximal connector flange (122) of slip ring assembly (120) includes a plurality of annular conductors (128) arranged substantially concentrically. The proximal face of distal connector flange (124) supports one or more electrical coupling members (130) each supporting a plurality of electrical contacts (not shown). Each electrical contact is positioned to contact a respective annular conductor (128) of proximal connector flange (122). Such an arrangement permits relative rotation between proximal connector flange (122) and distal connector flange (124) while maintaining electrical contact therebetween. Proximal connector flange (122) includes an electrical connector (132) extending proximally from a proximal face of proximal connector flange (122). Electrical connector (132) is configured to electrically couple annular conductors (128) with a shaft circuit board (134), shown schematically in FIG. 4, which may be mounted to shaft chassis (80) and include a microcontroller.

D. Attachment of Interchangeable Shaft Assembly to Handle Assembly

As described in greater detail below, interchangeable shaft assembly (14) is configured to be releasably coupled with handle assembly (12). It will be appreciated that various other types of interchangeable shaft assemblies having end effectors configured for various types of surgical procedures may be used in combination with handle assembly (12) described above.

As shown best in FIG. 4, a proximal end of tool chassis (80) of interchangeable shaft assembly (14) includes a pair of tapered attachment members (150) extending transversely to shaft axis (SA), and a shaft-side electrical connector (152) positioned therebetween. Shaft electrical connector (152) is in electrical communication with shaft circuit board (134) of shaft assembly (14). A distal end of handle frame (26) of handle assembly (12) includes a pair of dovetail receiving slots (154), and a handle-side electrical connector (156)

arranged therebetween. Handle electrical connector (156) is in electrical communication with handle circuit board (46) of handle assembly (12). During attachment of shaft assembly (14) to handle assembly (12), as described below, tapered attachment members (150) are received within dovetail receiving slots (154) along an installation axis (IA) that is transverse to shaft axis (SA). Additionally, shaft electrical connector (152) is electrically coupled with handle electrical connector (156). The proximal end of interchangeable shaft assembly (14) additionally includes a latch assembly (158) configured to releasably latch tool chassis (80) to handle frame (26) of handle assembly (12) when shaft assembly (14) is coupled with handle assembly (12).

As shown in FIG. 4, to attach interchangeable shaft assembly (14) to handle assembly (12), the clinician first aligns tapered attachment members (150) of tool chassis (80) with dovetail receiving slots (154) of handle frame (26). The clinician then moves shaft assembly (14) toward handle assembly (12) along installation axis (IA), thereby seating tapered attachment members (150) within dovetail receiving slots (154) and lockingly engaging latch assembly (158) with a distal portion of handle assembly (12). In doing so, attachment lug (94) of intermediate firing shaft (92) is also seated within cradle (56) of longitudinally movable drive member (48), thereby operatively coupling firing system (90) of shaft assembly (14) with firing drive system (40) of handle assembly (12). Additionally, proximal hooks (86) of closure shuttle (84) slide over and capture opposed lateral ends of attachment pin (34) extending from closure link (32), thereby operatively coupling the anvil closure components of shaft assembly (14) with closure drive system (30) of handle assembly (12). Additionally, during attachment of shaft assembly (14) with handle assembly (12), shaft electrical connector (152) on tool chassis (80) is electrically coupled with handle electrical connector (156) on handle frame (26), thereby placing shaft circuit board (134) of shaft assembly (14) in electrical communication with handle circuit board (46) of handle assembly (12).

In various examples, surgical instrument (10) may be further configured in accordance with one or more teachings of U.S. Pat. No. 9,345,481, entitled "Staple Cartridge Tissue Thickness Sensor System," issued May 24, 2016; U.S. Pat. No. 8,608,045, entitled "Powered Surgical Cutting and Stapling Apparatus With Manually Retractable Firing System," issued Dec. 17, 2013; U.S. Ser. No. 15/635,663, entitled "Method For Articulating A Surgical Instrument," filed Jun. 28, 2017; U.S. Ser. No. 15/635,631, entitled "Surgical Instrument With Axially Moveable Closure Member," filed Jun. 28, 2017; U.S. Ser. No. 15/635,837, entitled "Surgical Instrument Comprising An Articulation System Lockable To A Frame," filed Jun. 28, 2017; U.S. Pat. Pub. No. 2016/0066911, entitled "Smart Cartridge Wake Up Operation And Data Retention," published Mar. 10, 2016; U.S. Pat. Pub. No. 2015/0272575, entitled "Surgical Instrument Comprising A Sensor System," published Oct. 1, 2015; U.S. Pat. Pub. No. 2014/0263552, entitled "Staple Cartridge Tissue Thickness Sensor System," published Sep. 18, 2014; and/or U.S. Pat. Pub. No. 2014/0263541, entitled "Articulatable Surgical Instrument Comprising An Articulation Lock," published Sep. 18, 2014, the disclosures of which are incorporated by reference herein.

E. Exemplary End Effector with Sensors

In some instances, it may be desirable to provide the end effector of a surgical instrument with one or more sensors for sensing various operating conditions of the end effector. Such sensed conditions can then be communicated as electrical signals to a controller of the surgical instrument, such as a controller of shaft circuit board (134) and/or handle circuit board (46) of instrument (10) described above. The controller(s) may then take one or more actions in response to receiving such signals, such as providing one or more indications to the clinician operating the instrument.

Figure 8:
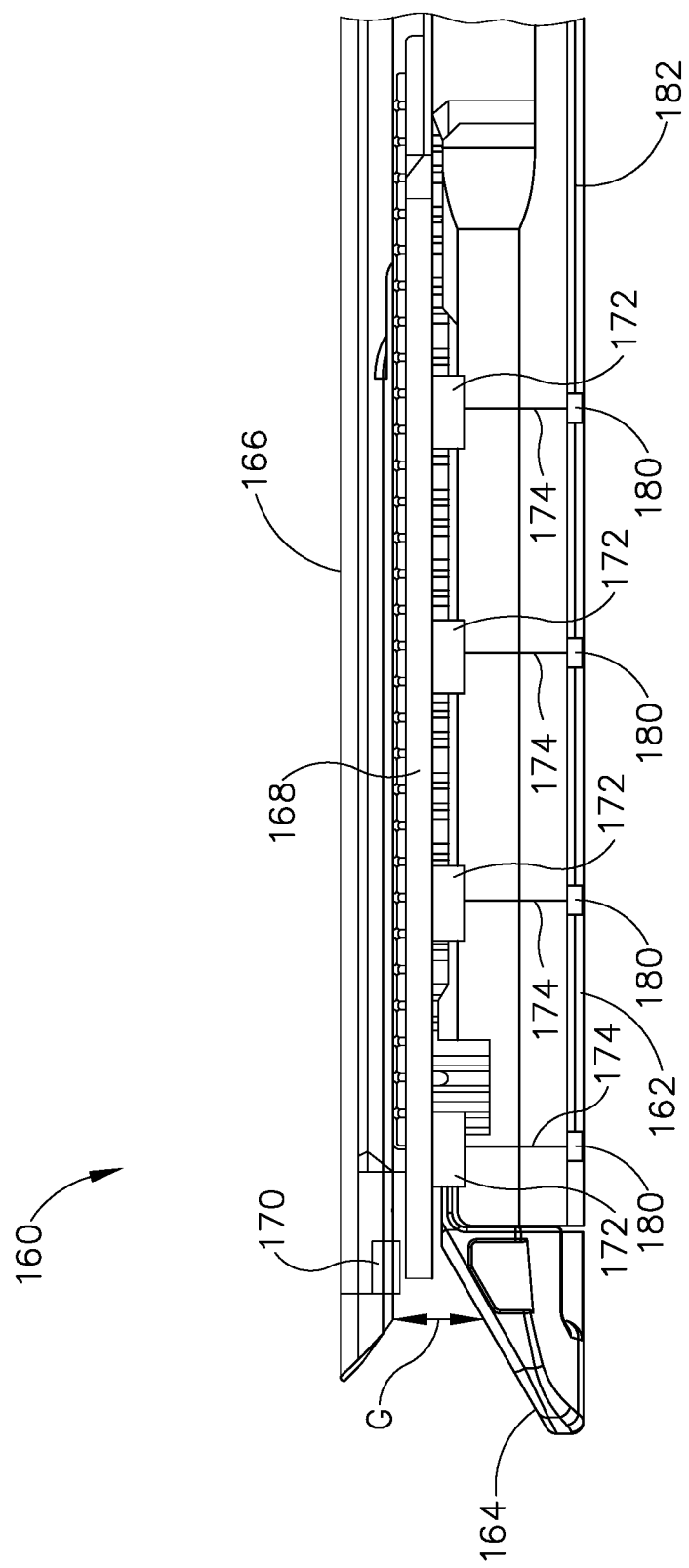
FIG. 8 depicts a side elevational view of another exemplary end effector having a plurality of sensors.

FIG. 8 illustrates an exemplary alternative end effector (160) suitable for use with surgical instrument (10) described above. End effector (160) is similar to end effector (16) described above in that end effector (160) includes a first jaw comprising an elongate channel (162) that receives a staple cartridge (164), and a second jaw comprising an anvil (166) configured to pivot relative to channel (162) between open and closed positions for clamping tissue (168) between anvil (166) and staple cartridge (164). Staple cartridge (164) may be similar to staple cartridge (72) described above.

End effector (160) differs from end effector (16) in that end effector (160) includes a first sensor (170) disposed on a tissue clamping side of anvil (166), and a plurality of second sensors (172) spaced along a length of channel (162). In other versions, one or more sensors, such as one or more of second sensors (172), may be provided on staple cartridge (164). In the present example, first sensor (170) is configured to detect one or more conditions of end effector (160), such as a gap (G) between anvil (166) and staple cartridge (164), which may correspond to a thickness of tissue (168) clamped by end effector (160). Second sensors (172) are also configured to detect one or more conditions of end effector (160) and/or of tissue (168) clamped by end effector (160). For instance, second sensors (172) may be configured to detect one or more conditions such as a color of staple cartridge (164), a length of staple cartridge (164), a clamping condition of end effector (160), and/or the number of actual and/or remaining uses of end effector (160) and/or staple cartridge (164), for example. While end effector (160) is shown having one first sensor (160) and four second sensors (172), various other suitable quantities and arrangements of sensors (170, 172) may be provided in other examples.

Each sensor (170, 172) may comprise any sensor type suitable for measuring the respective one or more conditions of end effector (160). For instance, each sensor (170, 172) may comprise a magnetic sensor (e.g., a Hall effect sensor), a strain gauge, a pressure sensor, an inductive sensor (e.g., an eddy current sensor), a resistive sensor, a capacitive sensor, or an optical sensor, for example. Each sensor (170, 172) is configured to communicate electrical signals corresponding to a sensed condition of end effector (160) to shaft circuit board (134), which may in turn communicate information based on the signals to handle circuit board (46), via slip ring assembly (120) described above.

It should be understood that channel (162) may selectively receive staple cartridge (164) such that staple cartridge (164) may be attached to channel (162), used in accordance with the description herein, removed from channel (162), and replaced with an unused, second staple cartridge (164). Therefore, in versions in which second sensors (172) are provided on staple cartridge (164), second sensors (172) may be configured to selectively establish an electrical connection with shaft circuit board (134) once staple cartridge (164) is suitably coupled to channel (162). In the current example, second sensors (172) each include an electrical contact (174), while channel (162) includes a plurality of electrical contacts (180). Corresponding contacts (174, 180) are dimensioned to electrically couple with each other when staple cartridge (164) is suitably coupled with channel (162). Additionally, channel (162) includes electrical traces (182) extending from contacts (180) all the way to electrical coupling member (130) of slip ring assembly (120). Therefore, when staple cartridge (164) is suitably coupled with channel (162), second sensors (172) are in electrical communication with shaft circuit board (134).

II. Exemplary Electrical Connection Assemblies

During use of surgical instrument (10) in surgical procedures, one or more of the electrical contacts of electrical connectors (152, 156) may be exposed to fluids, for example due to ingress of fluids proximally through shaft assembly (14). Such exposure to fluids could undesirably cause shorting of electrical pathways in surgical instrument (10), which could result in failure of one or more electrical systems of instrument (10).

The exemplary electrical connection assemblies described below provide various features configured to substantially block fluids from reaching the electrical contacts of one or both of handle assembly (12) and shaft assembly (14), and thereby prevent electrical shorting of the contacts. For instance, as described in greater detail below, some of these exemplary features may be in the form of electrically insulating barriers positioned between adjacent electrical contacts of a respective electrical connector. Other such features may be in the form of a membrane that covers a respective set of electrical contacts. Such features and others may be further configured to establish a liquid-tight seal that fully surrounds the electrical connection established between the electrical connectors when shaft assembly (14) is coupled to handle assembly (12). This liquid-tight seal further protects the electrical connection from unwanted exposure to fluids that might otherwise cause electrical shorting.

It will be understood that each exemplary electrical connection assembly described below is suitable for use with surgical instrument (10), for instance in place of electrical connectors (152, 156). As described in greater detail below, each electrical connection assembly includes a first electrical connector supported by a distally facing portion of handle frame (26) of handle assembly (12), and a mating second electrical connector supported by a proximally facing portion of tool chassis (80) of interchangeable shaft assembly (14). The first electrical connector includes a first connector body and a plurality of first electrical contacts supported by the first connector body. The second electrical connector includes a second connector body and a plurality of second electrical contacts supported by the second connector body. Each exemplary electrical connection assembly further includes one or more features configured to block fluids from reaching the electrical contacts of the connection assembly, thereby reducing the risk of electrical shorts. Throughout the exemplary configurations described below, the first and second electrical contacts may be of various suitable types known in the art, such as leaf spring contacts or spring-loaded pin contacts, for example.

A. Electrical Connection Assembly Having Actuatable Electrical Contacts

Figure 9:
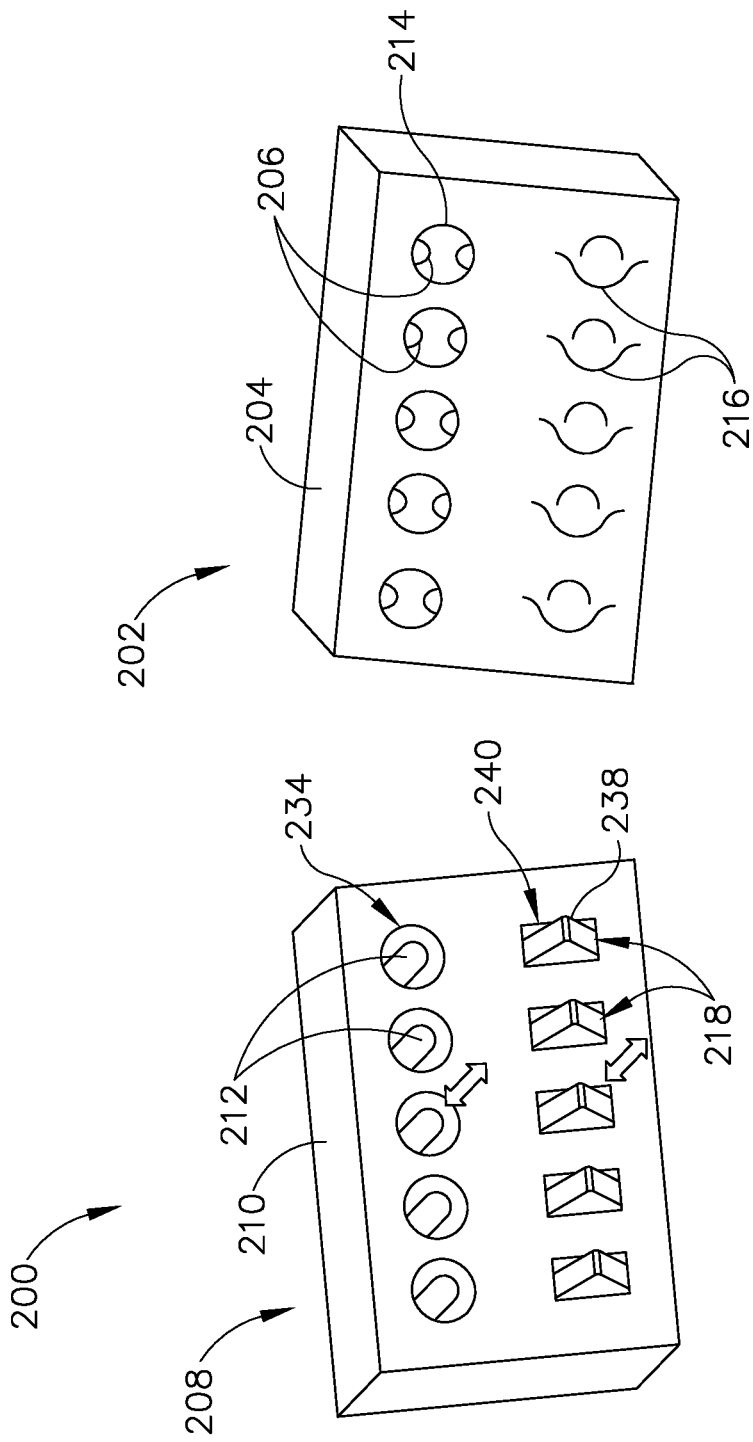
FIG. 9 depicts a schematic perspective view of an exemplary electrical connection assembly suitable for use with the surgical instrument of FIG. 1, showing first and second connectors of the connection assembly in a disengaged state.
Figure 11A:
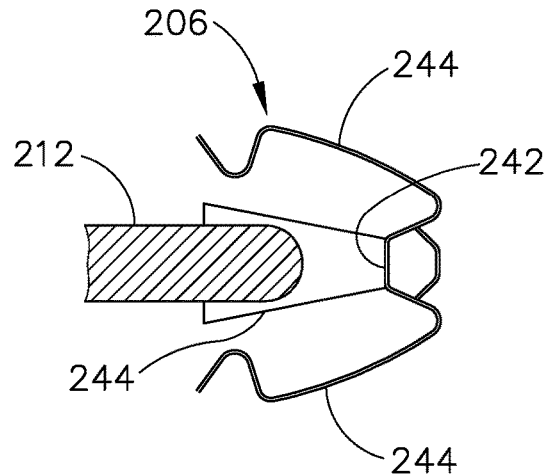
FIG. 11A depicts a side cross-sectional view of exemplary first and second electrical contacts of the electrical connection assembly of FIG. 9, showing the electrical contacts in a disengaged state.
Figure 12A:
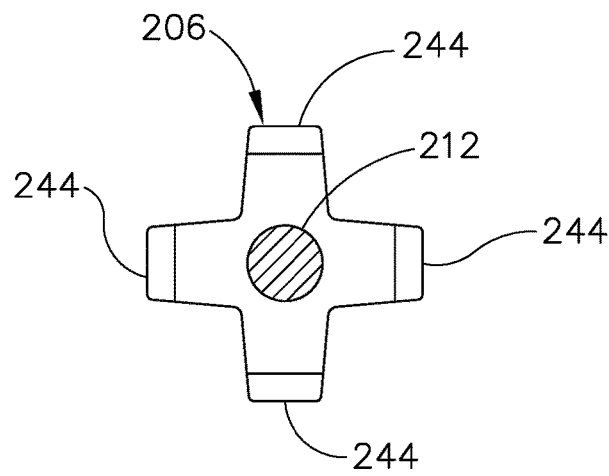
FIG. 12A depicts an end cross-sectional view of the first and second electrical contacts of FIG. 11A, showing the electrical contacts in a disengaged state.
Figure 11B:
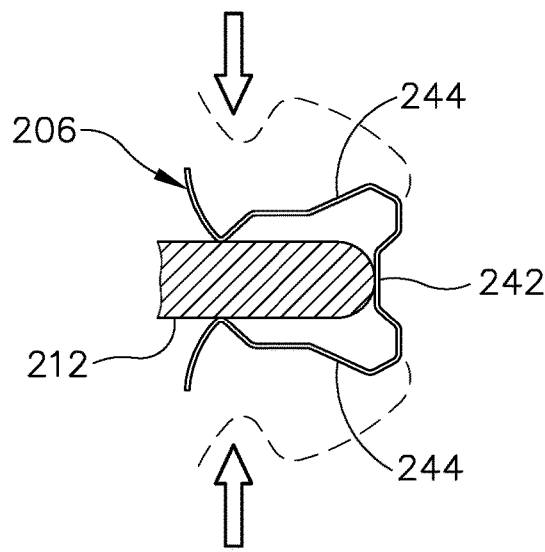
FIG. 11B depicts a side cross-sectional view of the first and second electrical contacts of FIG. 11A, showing the electrical contacts in an engaged state.
Figure 12B:
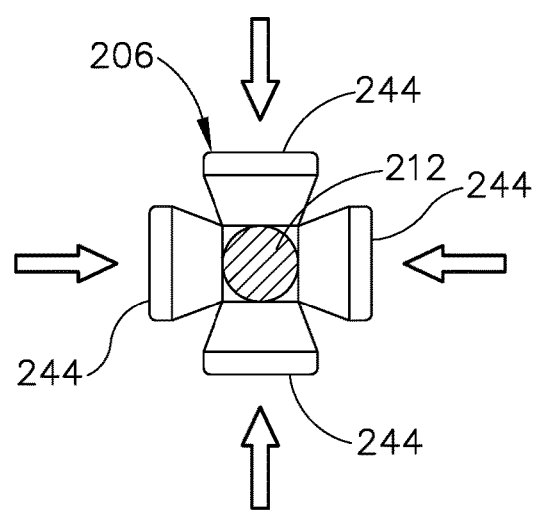
FIG. 12B depicts an end cross-sectional view of the first and second electrical contacts of FIG. 11B, showing the electrical contacts in an engaged state.

FIG. 9 shows a first exemplary electrical connection assembly (200) suitable for use with surgical instrument (10). Electrical connection assembly (200) includes a first electrical connector (202) that is supported by and is fixed relative to a distally facing portion of handle frame (26) of handle assembly (12). First electrical connector (202) includes a first connector body (204) and a plurality of first electrical contacts (206) fixed relative to first connector body (204). Connection assembly (200) further includes a second electrical connector (208) that is supported by and is fixed relative to a proximally facing portion of tool chassis (80) of shaft assembly (14). Second electrical connector (208) includes a second connector body (210) and a plurality of second electrical contacts (212) movably coupled with second connector body (210), as described in greater detail below. First electrical contacts (206) are in electrical communication with handle circuit board (46), and second electrical contacts (212) are in electrical communication with shaft circuit board (134). In other examples, a reverse configuration may be provided in which first electrical connector (202) is coupled to shaft assembly (14) and second electrical connector (208) is coupled to handle assembly (12).

As shown best in FIGS. 9-10B, first electrical connector (202) of the present example includes a plurality of recesses (214) spaced laterally across an upper portion of the distal face of first connector body (204). Each recess (214) houses a respective first electrical contact (206), such that first electrical contacts (206) are recessed proximally of the distal face of first connector body (204). First electrical contacts (206) are thus electrically insulated from one another by first connector body (204), which extends between each adjacent pair of first contacts (206) and thereby provides an electrically insulating barrier between adjacent first contacts (206). First electrical connector (202) further includes a plurality of engagement features shown in the form of rounded cam protrusions (216) that project distally from and are spaced laterally across a lower portion of the distal face of first connector body (204). In the present example, each cam protrusion (216) is aligned vertically with a respective recess (214) and a corresponding first electrical contact (206).

Second electrical connector (208) of the present example includes a plurality of levers (218) that are spaced laterally within an interior of second connector body (210). A medial portion of each lever (218) is pivotably coupled to second connector body (210) with a laterally extending pivot pin (220). Each lever (218) is configured to pivot relative to second connector body (210) between a first pivot position, shown in FIG. 10A, and a second pivot position, shown in FIG. 10B, in response to attachment of shaft assembly (14) to handle assembly (12), as described in greater detail below. In the present example, each lever (218) is configured to pivot independently in a respective vertical plane that extends parallel to installation axis (IA) (see FIG. 4). Additionally, each lever (218) is coupled to a resilient member shown in the form of a torsion spring (222) that biases lever (218) toward the first pivot position. In other versions, levers (218) may be coupled with one another such that levers (218) are configured to pivot together, dependently on one another.

Each lever (218) includes an upper end (224) that pivotably and translatably couples to the distal end of a plunger (226). A proximal end of plunger (226) supports an o-ring seal (228) and couples to a respective one of second electrical contacts (212) with a resilient member shown in the form of a compression spring (230). Each plunger (226) is configured to actuate proximally and distally, in a direction transverse to installation axis (IA), through a respective cylinder (232) when the respective lever (218) pivots between the first and second pivot positions. Each cylinder (232) is supported by second connector body (210) and defines an upper opening (234) through the proximal face of second connector body (210). In some examples, cylinders (232) may be formed integrally with second connector body (210). Each cylinder (232) is configured to function not only as a guide for the respective plunger (226), but also as an electrically insulating barrier for the respective second electrical contact (212). In examples in which each second electrical contact (212) is electrically coupled with its respective lever (218), levers (218) may be electrically insulated from one another by suitable structures within the interior of second connector (208), such as portions of second connector body (210)

Each lever (218) further includes an opposed lower end (236) that defines a follower feature (238) shown in the form of an angular protrusion. Follower protrusion (238) is configured to project proximally through a respective lower opening (240) formed in the proximal face of second connector body (210) when lever (218) is in the first pivot position (FIG. 10A). Each follower protrusion (238) is configured to engage a respective cam protrusion (216) of first electrical connector (202) when shaft assembly (14) is translated into engagement with handle assembly (12) along installation axis (IA), as described in greater detail below. This provides a camming engagement between protrusions (216, 238) that urges lever (218) from the first pivot position to the second pivot position as shaft assembly (14) is fully seated with handle assembly (12).

FIG. 10A shows first electrical connector (202) positioned in confronting relation with second electrical connector (208) as the proximal end of shaft assembly (14) is initially engaged with the distal end of handle assembly (12) along installation axis (IA). At this stage, levers (218) of second electrical connector (208) are held in the first pivot position by torsion springs (222), such that plungers (226) and second electrical contacts (212) are positioned distally within cylinders (232), and such that follower protrusions (238) project proximally through lower openings (240) of second connector body (210). Accordingly, at this stage, first electrical contacts (206) are recessed within first connector body (204) and are thus electrically insulated from one another. Similarly, second electrical contacts (212) are recessed within second connector body (210), via cylinders (232), and are thus electrically insulated from one another. Advantageously, this configuration protects against any electrical shorting of electrical contacts (206, 212) that might otherwise result in the presence of fluid on the mating ends of handle assembly (12) and/or shaft assembly (14).

As shown in FIG. 10B, as the distal end of shaft assembly (14) fully translates downwardly along installation axis (IA) and seats with the proximal end of handle assembly (12), upper openings (234) of second electrical connector (208) pass into alignment with respective recesses (214) of first electrical connector (202). Simultaneously, cam protrusions (216) of first connector (202) engage respective follower protrusions (238) of second connector (208), thereby urging levers (218) to pivot from the first pivot position to the second pivot position. As each lever (218) pivots about its pivot pin (220), upper end (224) of lever (218) drives the respective plunger (226) and second electrical contact (212) proximally through the respective cylinder (232) and into the opposing recess (214) of second electrical connector (208). In the present example, the distal tip of each second electrical contact (212) exerts a proximally directed force on an inner base portion (242) of the respective first electrical contact (206), thereby causing first electrical contact (206) to collapse and clamp against second electrical contact (212), as described in greater detail below. This engagement establishes an electrical connection between first and second electrical contacts (206, 212). Simultaneously, o-ring seal (228) of plunger (226) passes into and sealingly engages the distal end of recess (214), thereby creating a liquid-tight seal that protects the electrical connection from exposure to fluids that might otherwise cause electrical shorting.

During subsequent detachment of shaft assembly (14) from handle assembly (12), second electrical connector (208) is translated vertically relative to first electrical connector along installation axis (IA) such that cam protrusions (216) disengage follower protrusions (238). This disengagement allows levers (218) to return to their first pivot positions and withdraw first electrical contacts (206) from second electrical contacts (212) and recesses (214).

FIGS. 11A-12B show additional details of first and second electrical contacts (206, 212) of electrical connection assembly (200) described above. In the present example, first electrical contacts (206) are shown in the form of spring clips, and second electrical contacts (212) are shown in the form of proximally extending pins. Each spring clip (206) has a raised base (242) that is oriented proximally, and a plurality of spring arms (244) extending distally from raised base (242). While four spring arms (244) are shown in the present example, various other quantities of spring arms (244) may be provided in other examples. When first and second electrical connectors (202, 208) are coupled together in the manner described above, the distal tip of each pin (212) compresses raised base (242) of the respective spring clip (206) proximally, thereby causing spring arms (244) to collapse inwardly and clamp against pin (212). Each spring clip (206) is biased toward the expanded configuration shown in FIGS. 11A and 12A, such that spring arms (244) release pin (212) upon distal retraction of pin (212) from spring clip (206).

B. Electrical Connection Assembly Having Rotating Electrical Contacts

FIG. 13 shows another exemplary electrical connection assembly (250) suitable for use with surgical instrument (10). Electrical connection assembly (250) includes a first electrical connector (252) that is supported by and is fixed relative to a distally facing portion of handle frame (26) of handle assembly (12). First electrical connector (252) includes a first connector body (254) and a plurality of first electrical contacts (256) fixed relative to first connector body (254). Connection assembly (250) further includes a second electrical connector (258) that is supported by and is fixed relative to a proximally facing portion of tool chassis (80) of shaft assembly (14). Second electrical connector (258) includes a second connector body (260) and a plurality of second electrical contacts (262) (see FIG. 14) movably coupled with second connector body (260), as described in greater detail below. First electrical contacts (256) are in electrical communication with handle circuit board (46), and second electrical contacts (262) are in electrical communication with shaft circuit board (134). In other examples, a reverse configuration may be provided in which first electrical connector (252) is coupled to shaft assembly (14) and second electrical connector (258) is coupled to handle assembly (12).

First electrical connector (252) of the present example includes a distally projecting ledge (264) that extends laterally across an upper portion of a distal face of first connector body (254). In other versions, ledge (264) may be presented in the form of a plurality of individual ledges, each aligned vertically with a respective one of first electrical contacts (256). First electrical contacts (256) of the present example are shown in the form of spring contacts spaced laterally across a lower portion of the distal face of first connector body (204), and project distally from the distal face. In other examples, first electrical contacts (256) may be recessed within first connector body (254).

Second electrical connector (258) of the present example rotatably supports a plurality of spiral-shaped rotating elements (266) to which second electrical contacts (262) are mounted, as shown in FIG. 14. Rotating elements (266) are housed within second connector body (260) such that rotating elements (266) are oriented vertically and are spaced apart laterally. Each rotating element (266) includes an inner spiral end (268) and an outer spiral end (270). A cleaning element (272), which may include an abrasive material such as steel wool for example, is fixed to an outwardly facing surface of each rotating element (266) at a location adjacent to inner spiral end (268). A second electrical contact (262) is fixed to the outwardly facing surface on a curved portion of rotating element (266) located between cleaning element (272) and outer spiral end (270). In the present example, second electrical contact (262) is mounted to rotating element (266) such that at least a portion of second contact (262) is offset from outer spiral end (270) by approximately 90 degrees. As described in greater detail below, each rotating element (266) is biased toward a first rotational position by a resilient member (not shown).

Each rotating element (266) of the present example is configured to rotate independently relative to second connector body (260). In other versions, rotating elements (266) may be alternatively configured such that second electrical contacts (262) rotate together. For instance, FIG. 15 shows an exemplary alternative configuration in which second electrical contacts (262) are mounted to the curved outer surface of a single rotating structure (274). Rotating structure (274) is mounted to a central pin (276) that enables rotation of structure (274) relative to second connector body (260). Rotating structure (274) includes a curved, outwardly projecting arm (278) that is configured to engage ledge (264) of first electrical connector (252) and thereby rotate structure (274) about pin (276) in a manner similar to rotating elements (266), as described below. A torsion spring (279) may be mounted to central pin (276) to bias rotating structure (274) toward a first rotational position similar to the first position of rotating elements (266), described below.

As shown in FIG. 13, second electrical connector (258) of the present example further includes a sealing layer in the form of a membrane (280) mounted to the proximal face of second connector body (260). As described below, membrane (280) is configured to be breached by rotating elements (266) during attachment of shaft assembly (14) to handle assembly (12). In the present example, membrane (280) includes a plurality of pre-formed vertical slits (282) that facilitate such breach and ensure that only select features of second connector (258) are exposed from behind membrane (280) during use. For instance, as shown in FIG. 13, only outer spiral ends (270) of rotating elements (266) breach through slits (282) when rotating elements (266) are in their first rotational positions, thus positioning outer spiral ends (270) for engagement with ledge (264) of handle assembly (12) as described below. In this manner, membrane (280) shields second electrical contacts (262) from exposure to fluids that might otherwise cause electrical shorting, and maintains second electrical contacts (262) in a covered state until rotating elements (266) rotate to expose second contacts (262) for engagement with first electrical contacts (256). Membrane (280) may be formed of any suitable material, such as an elastomeric material. In some versions, pre-formed slits (282) may be omitted from membrane (280), and rotating elements (266) may be configured to puncture through membrane (280) as rotating elements (266) rotate relative to second connector body (260).

Figure 16:
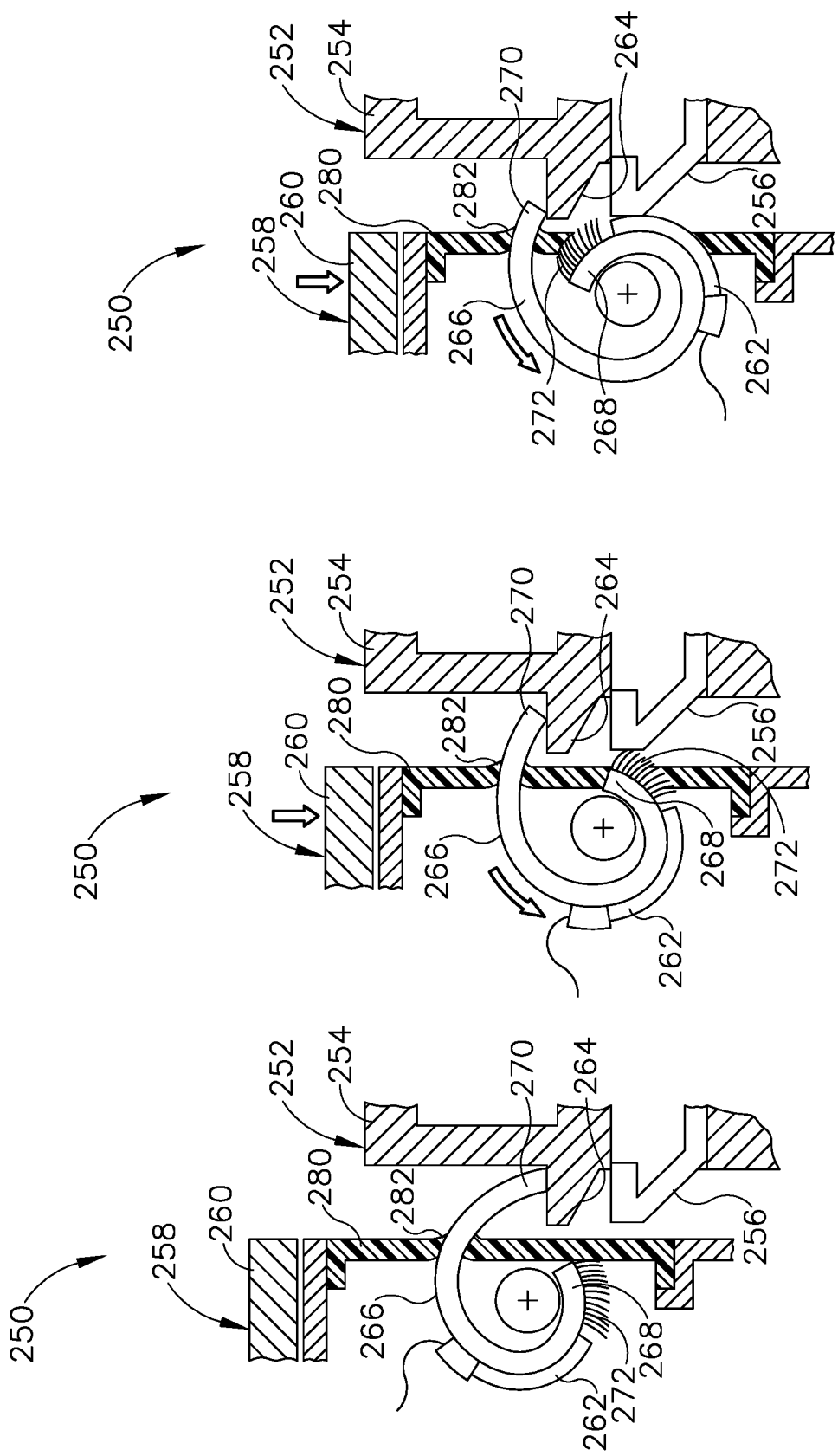
FIG. 16A depicts a side cross-sectional view of the first and second connectors of FIG. 13, showing the rotating elements in a first rotational position relative to the connectors.
FIG. 16B depicts a side cross-sectional view of the first and second connectors of FIG. 16A, showing the rotating elements in a second rotational position relative to the connectors.
FIG. 16C depicts a side cross-sectional view of the first and second connectors of FIG. 16B, showing the rotating elements in a third rotational position in which electrical contacts of the second connector electrically couple with electrical contacts of the first connector.

FIG. 16A shows first electrical connector (202) positioned in confronting relation with second electrical connector (258) as the proximal end of shaft assembly (14) is initially engaged with the distal end of handle assembly (12) along installation axis (IA). At this stage, rotating structures (272) of second electrical connector (258) remain resiliently biased in their first rotational position such that only outer spiral ends (270) project proximally through membrane (280). As shown in FIG. 16A, as shaft assembly (14) is lowered along installation axis (IA), outer spiral ends (270) engage an upper surface of ledge (264) of first electrical connector (252). As shown in FIG. 16B, continued advanced of shaft assembly (14) along installation axis (IA) causes ledge (264) to drive rotation of rotating elements (266) relative to second connector body (260) so that cleaning elements (272) become exposed through slits (282) of membrane (280). Each cleaning element (272) engages and thereby cleans a respective first electrical contact (256) of first connector (252) so as to remove any fluid or other substance that might interfere with proper electrical coupling between first and second electrical connectors (302, 258).

As shown in FIG. 16C, continued advanced of shaft assembly (14) downwardly along installation axis (IA) causes ledge (264) to rotate rotating elements (266) further so that second electrical contacts (262) become exposed through membrane (280) and rotate into engagement with first electrical contacts (256). Rotating elements (266) and ledge (264) may be configured to require any suitable degree of rotation of rotating elements (266) relative to second connector body (260), for example approximately 90 degrees, to achieve engagement of electrical contacts (256, 262). Accordingly, similar to second electrical contacts (212) of electrical connection assembly (200), second electrical contacts (262) actuate from a recessed position to an extended position in response to attachment of shaft assembly (14) to handle assembly (12). This feature, in combination with cleaning elements (272), ensures that electrical contacts (256, 262) are protected from exposure to fluids that might otherwise cause electrical shorting.

In some versions of electrical connection assembly (250), first electrical connector (252) and/or or second electrical connector (258) may further include a sealing element configured to establish a liquid-tight seal that fully surrounds the electrical connections formed between first and second electrical contacts (256, 262). For instance, membrane (280) may be configured to sealingly engage at least the lower portion of the distal face of first connector body (254) when shaft assembly (14) is fully seated with handle assembly (12). In this manner, membrane (280) may block fluids from reaching joined electrical contacts (256, 262) and thereby protect the electrical connections from shorting.

Figure 17:
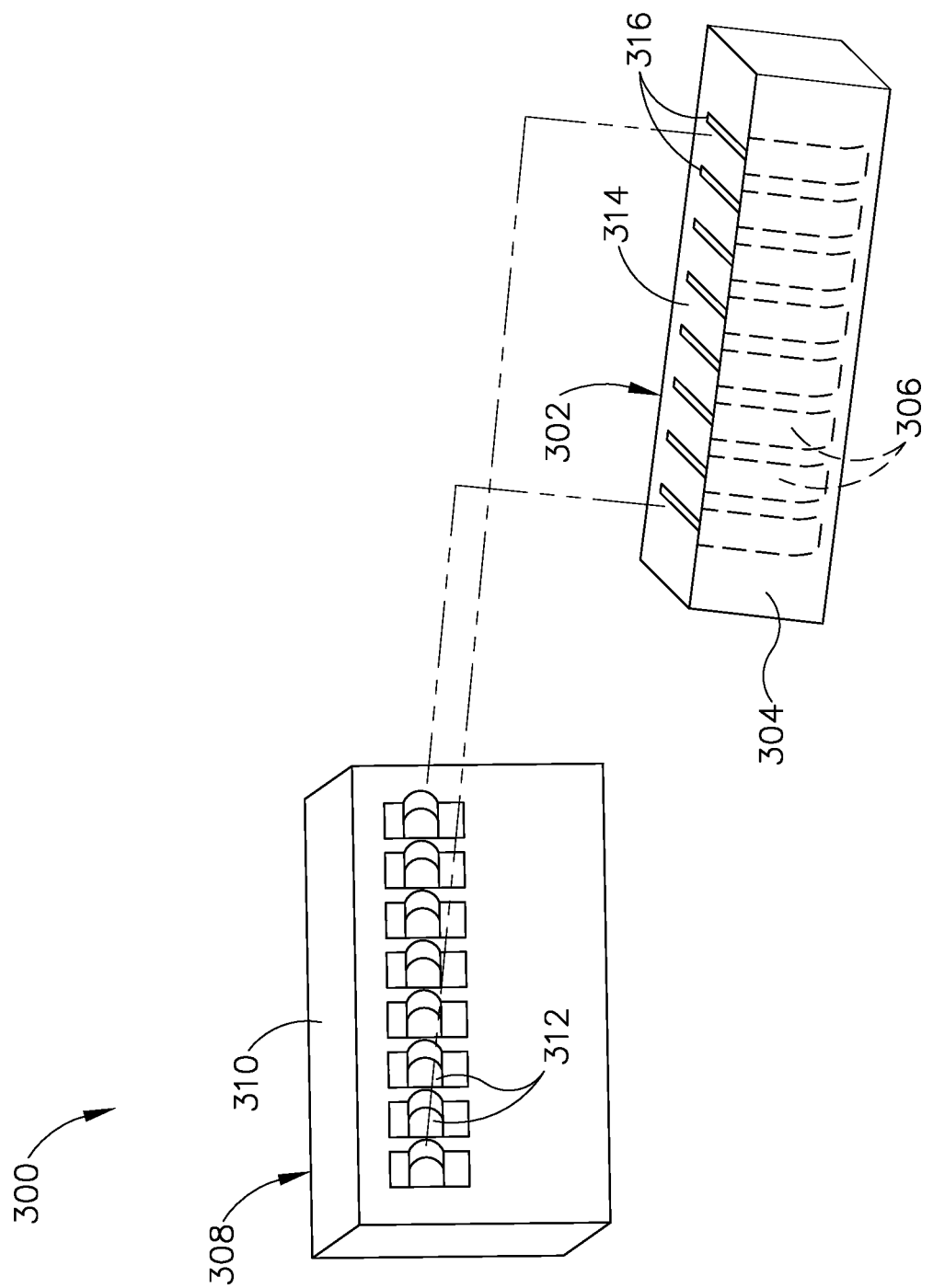
FIG. 17 depicts a schematic perspective view of another exemplary electrical connection assembly suitable for use with the surgical instrument of FIG. 1, showing first and second connectors of the connection assembly in a disengaged state.

C. Electrical Connection Assembly Having Compressible Connector Body and Sealing Membrane FIG. 17 shows another exemplary electrical connection assembly (300) suitable for use with surgical instrument (10). Electrical connection assembly (300) includes a first electrical connector (302) that is supported by and is fixed relative to a distally facing portion of handle frame (26) of handle assembly (12). First electrical connector (302) includes a first connector body (304) and a plurality of first electrical contacts (306) fixed relative to first connector body (304). Connection assembly (300) further includes a second electrical connector (308) that is supported by and is fixed relative to a proximally facing portion of tool chassis (80) of shaft assembly (14). Second electrical connector (308) includes a second connector body (310) and a plurality of second electrical contacts (312) fixed relative to second connector body (310). First electrical contacts (306) are in electrical communication with handle circuit board (46), and second electrical contacts (312) are in electrical communication with shaft circuit board (134). In other examples, a reverse configuration may be provided in which first electrical connector (302) is coupled to shaft assembly (14) and second electrical connector (308) is coupled to handle assembly (12).

First connector body (304) of the present example houses first electrical contacts (306) such that first contacts (306) are recessed therein, relative to at least upper and distal sides of first electrical connector (302). Further, first connector body (304) is formed of a flexible elastomeric material, such that first connector body (304) is configured to compress and expose first electrical contacts (306) when first connector body (304) is engaged by second electrical connector (308), as described in greater detail below. A sealing layer in the form of a membrane (314) is mounted to an open upper end of first connector body (304) and defines the upper side of first electrical connector (302). Membrane (314) is configured to protect first electrical contacts (306) from exposure to fluids that might otherwise cause electrical shorting between adjacent contacts (306), both before and after shaft assembly (14) is attached to handle assembly (12). As described below, membrane (314) is configured to be breached by second electrical contacts (312) during attachment of shaft assembly (14) to handle assembly (12). Membrane (314) includes a plurality of pre-formed longitudinal slits (316) that facilitate such breach, while ensuring that first electrical contacts (306) remain substantially covered and protected from exposure to fluids. In the present example, each slit (316) through a distal edge of membrane (314).

Second connector body (310) of the present example supports second electrical contacts (312) such that second contacts (312) project proximally from a proximal face of second electrical connector (308). Second electrical contacts (312) are spaced laterally from one another such that a portion of second connector body (310) extends between each adjacent pair of second contacts (312), thereby providing an electrically insulating barrier that reduces the risk of electrical shorting between adjacent contacts (312). Each second electrical contact (312) is configured to align with a respective membrane slit (316) of first electrical connector (302) during assembly, as described below.

Figure 18A:
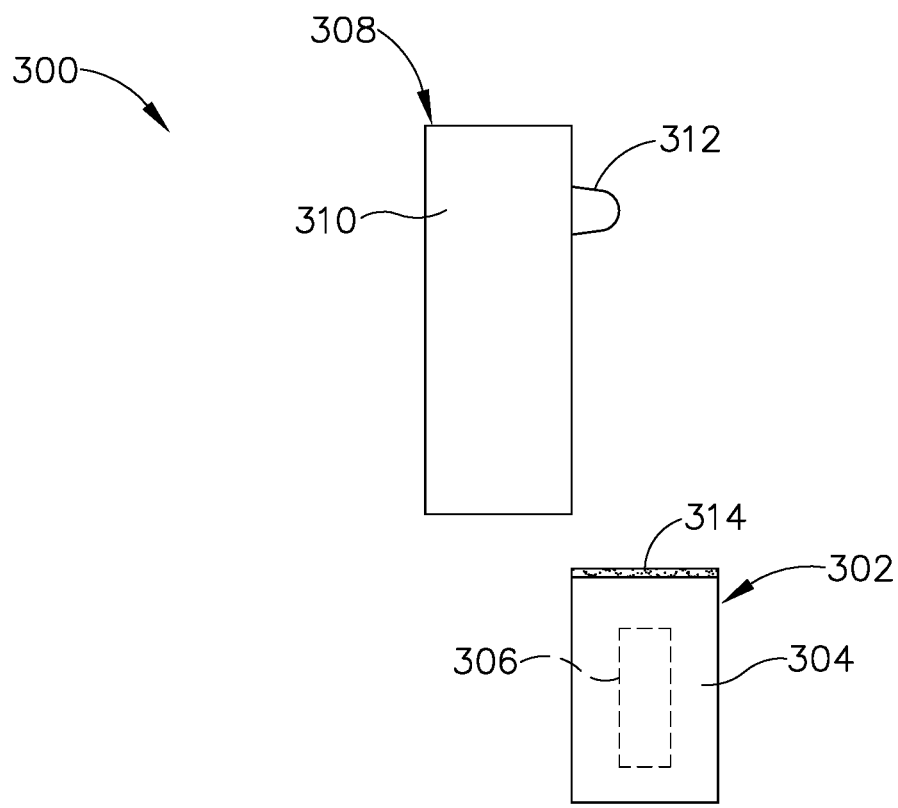
FIG. 18A depicts a schematic side view of the first and second connectors of FIG. 17, showing the connectors in a disengaged state.
Figure 18B:
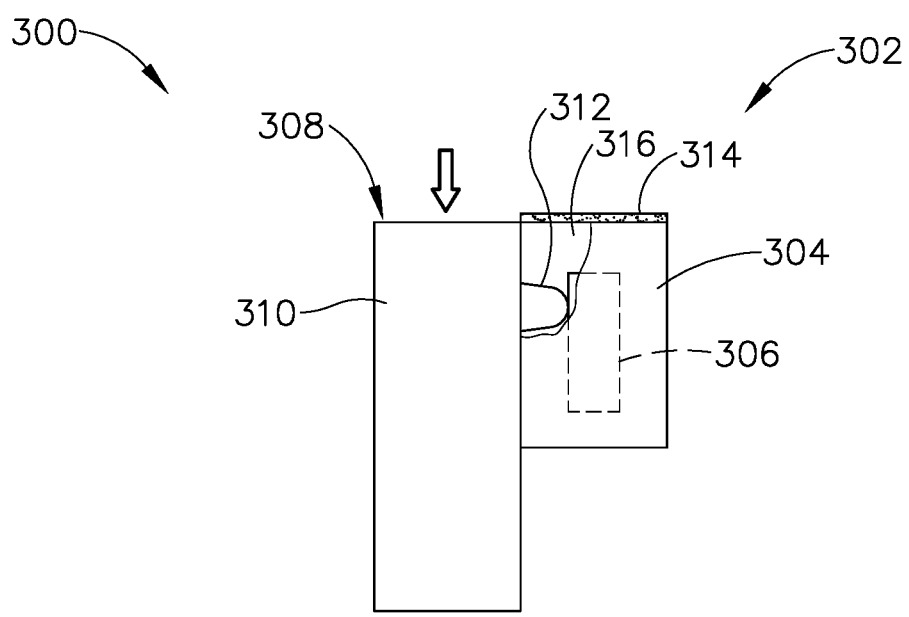
FIG. 18B depicts a schematic side view of the first and second connectors of FIG. 18A, showing the connectors in an engaged state.

FIG. 18A shows second electrical connector (308) positioned vertically above first electrical connector (302) as the proximal end of shaft assembly (14) is initially aligned with the distal end of handle assembly (12) along installation axis (IA). In this state, first electrical contacts (306) remain recessed within first connector body (304), and second electrical contacts (312) protrude proximally from second connector body (310). As shown in FIG. 18B, as shaft assembly (14) is advanced downwardly along installation axis (IA), second electrical contacts (312) breach through respective slits (316) of membrane (314) and project proximally into first connector body (304) to thereby compress at least the distal wall of first connector body (304) downwardly and proximally. This compression of first connector body (304) exposes first electrical contacts (306) for engagement with second electrical contacts (312). As second electrical contacts (312) breach through membrane slits (316), membrane (314) may wipe any fluids from second contacts (312) to prevent such fluids from entering first connector body (304) and causing electrical shorting of adjacent electrical contacts (306, 312).

As shaft assembly (14) fully seats with handle assembly (12), second electrical contacts (306, 312) couple together to establish an electrical connection. Simultaneously, compressible first connector body (304) may sealingly engage the proximal face of second connector body (310) to establish a liquid-tight seal that substantially surrounds the joined electrical contacts (306, 312) in a vertical plane that extends parallel to installation axis (IA). A distal edge of membrane (314) may also sealingly engage the proximal face of second connector body (310) to complete the liquid-tight seal around the joined contacts (306, 312) and thereby protect the electrical connection from exposure to fluids. In some versions, membrane slits (316) may extend downwardly through the distal face of first connector body (304) to facilitate receipt of second electrical contacts (312) therein with minimal or no compression of first connector body (304). This would also enable the distal face of first connector body (304) to establish a liquid-tight seal with second connector body that fully surrounds the joined electrical contacts (306, 312).

Figure 19A:
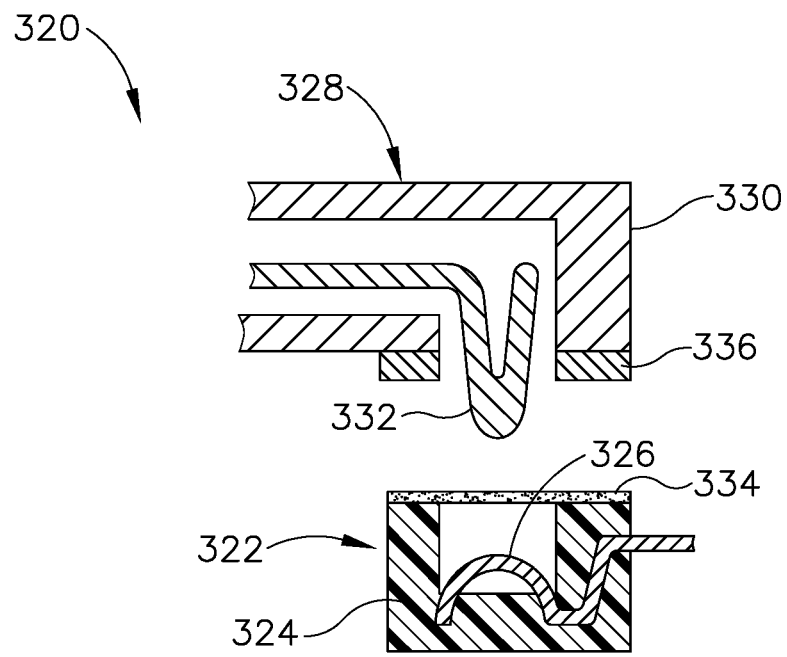
FIG. 19A depicts a side cross-sectional view of another exemplary electrical connection assembly suitable for use with the surgical instrument of FIG. 1, showing first and second connectors of the connection assembly in a disengaged state.
Figure 19B:
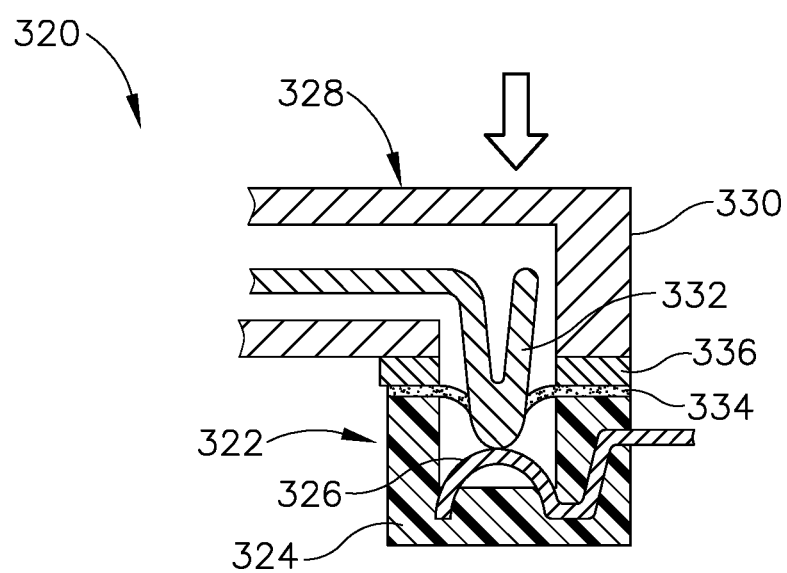
FIG. 19B depicts a side cross-sectional view of the electrical connection assembly of FIG. 19A, showing the first and second connectors in an engaged state.

D. Electrical Connection Assembly Having Sealing Membrane and Compressible Sealing Element FIGS. 19A and 19B show another exemplary electrical connection assembly (320) suitable for use with surgical instrument (10). Electrical connection assembly (320) includes a first electrical connector (322) that is supported by and is fixed relative to a distally facing portion of handle frame (26) of handle assembly (12). First electrical connector (322) includes a first connector body (324) and a plurality of first electrical contacts (326) fixed relative to first connector body (324). Connection assembly (320) further includes a second electrical connector (328) that is supported by and is fixed relative to a proximally facing portion of tool chassis (80) of shaft assembly (14). Second electrical connector (328) includes a second connector body (330) and a plurality of second electrical contacts (332) fixed relative to second connector body (330). First electrical contacts (326) are in electrical communication with handle circuit board (46), and second electrical contacts (332) are in electrical communication with shaft circuit board (134). In other examples, a reverse configuration may be provided in which first electrical connector (322) is coupled to shaft assembly (14) and second electrical connector (328) is coupled to handle assembly (12).

As shown in FIG. 19A, first connector body (324) of the present example houses first electrical contacts (326) such that first contacts (326) are recessed therein, and are spaced apart laterally. A sealing layer in the form of a membrane (334) is mounted to an open upper end of first connector body (324) and defines the upper side of first electrical connector (322). Membrane (334) is similar to membrane (314) described above in that membrane (334) is configured to protect first electrical contacts (326) from exposure to fluids both before and after attachment of shaft assembly (14) to handle assembly (12). As described below, membrane (334) is configured to be breached by second electrical contacts (332) during attachment of shaft assembly (14) to handle assembly (12). Though not shown, membrane (334) may include a plurality of pre-formed longitudinal slits configured to facilitate such breach, while ensuring that first electrical contacts (326) remain substantially covered and protected from exposure to fluids. In some examples, first electrical connector (322) may further include electrically insulating barriers, which may be provided by first connector body (324), arranged between adjacent pairs of first electrical contacts (326).

Second connector body (330) partially houses second electrical contacts (332), such that a tip of each second electrical contact (332) projects downwardly through an open lower side of second connector body (330). In some examples, portions of second connector body (330) may extend between each adjacent pair of second electrical contacts (332) so as to provide electrically insulating barriers, and such that each second electrical contact (332) projects downwardly through a respective opening. In other examples, the lower side of second connector body (330) may include a single opening that extends laterally and exposes each of the second electrical contacts (332).

Second electrical connector (328) of the present example further includes a compressible sealing element (336) mounted to the lower side of second connector body (330). Sealing element (336) is formed of a flexible elastic elastomeric material, such as santoprene for example, and is configured to compress against and thereby sealingly engage first connector body (324) when shaft assembly (320) is attached to handle assembly (320), as described below. In other versions, sealing element (336) may be mounted to the upper side of first connector body, or a sealing element (336) may be provided on each of the upper side of first connector body (324) and the lower side of second connector body (330). In still other versions, one or both of first connector body (324) and second connector body (330) may be formed of a compressible material configured to compress against and thereby sealingly engage the opposing connector body (324, 330).

FIG. 19A shows second electrical connector (328) positioned vertically above first electrical connector (322) as the proximal end of shaft assembly (14) is initially aligned with the distal end of handle assembly (12) along installation axis (IA). In this state, first electrical contacts (326) remain recessed within first connector body (324), and second electrical contacts (332) project downwardly from second connector body (330). As shown in FIG. 19B, as shaft assembly (320) is advanced downwardly along installation axis (IA), second electrical contacts (332) breach downwardly through membrane (334), for example via respective slits (not shown), and project downwardly into first connector body (324) to electrically couple with first electrical contacts (326). As second electrical contacts (332) pass through membrane (334), membrane (334) may wipe any fluid from second electrical contacts (332) to prevent such fluid from entering first connector body (324) and causing electrical shorting between adjacent electrical contacts (326, 332). As second electrical connector (328) fully seats with first electrical connector (322), compressible sealing element (336) sealingly engages the upper side of first connector body (324), thereby forming a liquid-tight seal that fully surrounds the electrical connection in a horizontal plane that extends transversely to installation axis (IA). This liquid-tight seal protects the electrical connection from unwanted exposure to fluids that might otherwise cause electrical shorting. Additionally, the formation of the liquid-tight seal in a plane transverse to installation axis (IA) eliminates application of shearing forces on sealing element (336) during engagement of first and second electrical connectors (322, 328).

E. Electrical Connection Assembly Having Corrugated Sealing Membrane

FIGS. 20A and 20B show another exemplary electrical connection assembly (340) suitable for use with surgical instrument (10). Electrical connection assembly (340) includes a first electrical connector (342) that is supported by and is fixed relative to a distally facing portion of handle frame (26) of handle assembly (12). First electrical connector (342) includes a first connector body (344) and a plurality of first electrical contacts (346) fixed relative to first connector body (344). Connection assembly (340) further includes a second electrical connector (348) that is supported by and is fixed relative to a proximally facing portion of tool chassis (80) of shaft assembly (14). Second electrical connector (348) includes a second connector body (350) and a plurality of second electrical contacts (352) fixed relative to second connector body (350). First electrical contacts (346) are in electrical communication with handle circuit board (46), and second electrical contacts (352) are in electrical communication with shaft circuit board (134). In other examples, a reverse configuration may be provided in which first electrical connector (342) is coupled to shaft assembly (14) and second electrical connector (348) is coupled to handle assembly (12). In the present example, first electrical contacts (346) are shown in the form of female contacts, and second electrical contacts (352) are shown in the form of male contacts configured to be inserted into female contacts (346).

Electrical connection assembly (340) further includes a sealing layer in the form of a corrugated membrane (354) having a plurality of corrugations (356) arranged laterally in alignment with first and second electrical contacts (346, 352). Corrugated membrane (354) is configured to be positioned between first electrical contacts (346) and second electrical contacts (352) such that each corrugation (356) aligns with a respective pair of first and second electrical contacts (346, 352). Corrugated membrane (354) may be coupled to first connector body (344) in some examples, or to second connector body (350) in other examples, so as to protect the respective set of electrical contacts (346, 352) from exposure to fluids both before and after attached of shaft assembly (14) to handle assembly (12), in a manner similar to membranes (280, 314, 334) described above. Each corrugation (356) is configured to be breached by a respective second electrical contact (352) during engagement of first and second electrical connectors (342, 348), as described below. In some versions, each corrugation (356) may include a slit at its lower tip that facilitates breach of second electrical contact (352) through corrugation (356), such that each corrugation (356) is generally in the form of a duckbill seal.

FIG. 20A shows second electrical connector (348) positioned vertically above first electrical connector (342) as the proximal end of shaft assembly (14) is initially aligned with the distal end of handle assembly (12) along installation axis (IA). Each second electrical contact (352) is aligned with a respective corrugation (356) of corrugated membrane (354). As shown in FIG. 20B, as shaft assembly (340) is advanced downwardly along installation axis (IA), each second electrical contact (352) breaches downwardly through a respective membrane corrugation (356) and is received by a respective first electrical contact (346) to establish an electrical connection therebetween. As shown in FIG. 20B, corrugations (356) separate the individual electrical connections from one another, thereby acting as electrically insulating barriers that protect the electrical connections from exposure to fluids that might otherwise induce electrical shorting between adjacent contacts (346, 352). In some versions, electrical connection assembly (340) may further include one or more sealing elements similar to those described above in connection with electrical connection assemblies (300, 320).

F. Electrical Connection Assembly Having Male and Female Coupling Features

Figure 21:
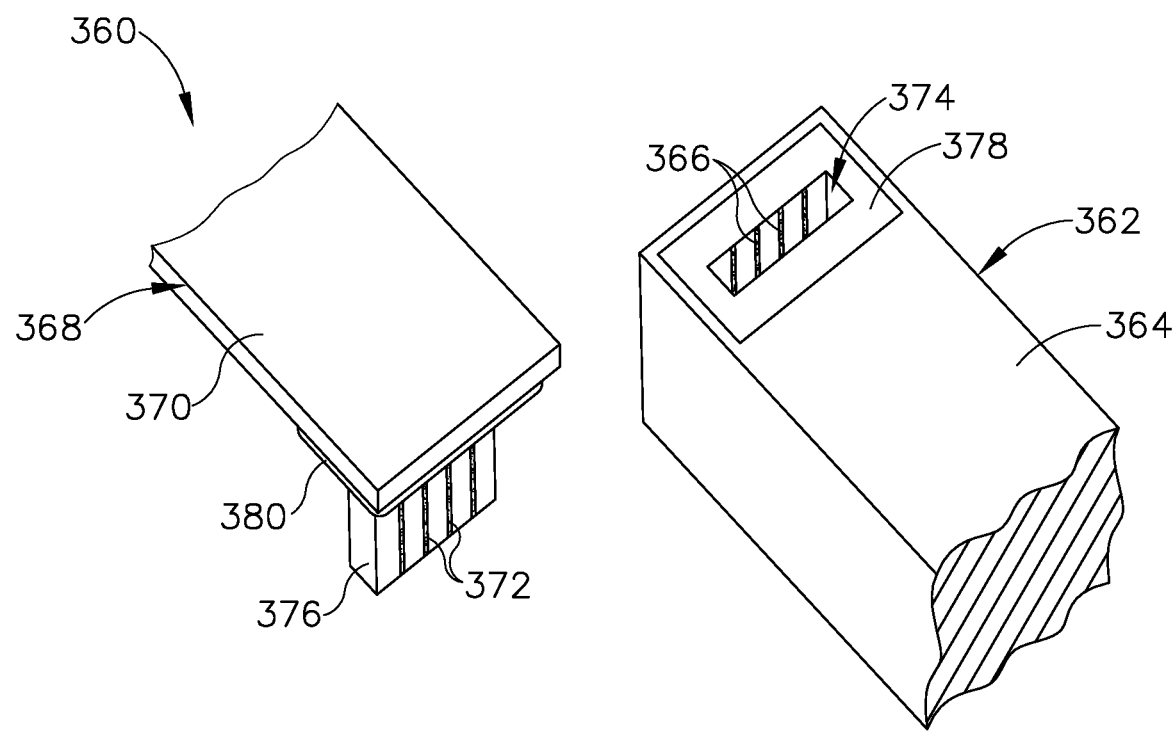
FIG. 21 depicts a perspective view of another exemplary electrical connection assembly suitable for use with the surgical instrument of FIG. 1, showing first and second connectors of the connection assembly in a disengaged state.
Figure 22:
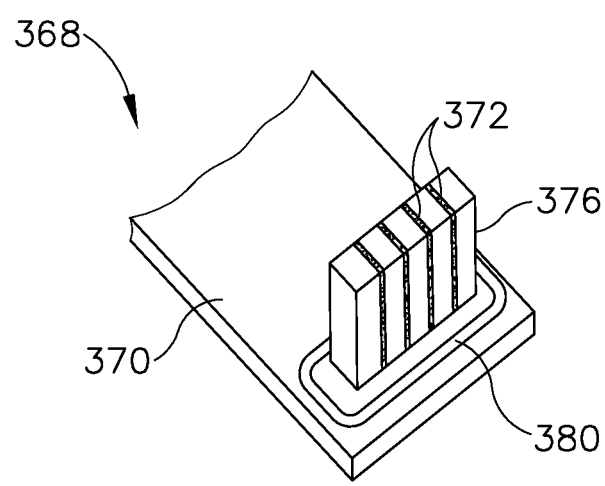
FIG. 22 depicts a perspective view of an underside of the second connector of FIG. 21.

FIG. 21 shows another exemplary electrical connection assembly (360) suitable for use with surgical instrument (10). Electrical connection assembly (360) includes a first electrical connector (362) that is supported by and is fixed relative to a distally facing portion of handle frame (26) of handle assembly (12). First electrical connector (362) includes a first connector body (364) and a plurality of first electrical contacts (366) fixed relative to first connector body (364). Connection assembly (360) further includes a second electrical connector (368) that is supported by and is fixed relative to a proximally facing portion of tool chassis (80) of shaft assembly (14). Second electrical connector (368) includes a second connector body (370) and a plurality of second electrical contacts (372) fixed relative to second connector body (370). First electrical contacts (366) are in electrical communication with handle circuit board (46), and second electrical contacts (372) are in electrical communication with shaft circuit board (134). In other examples, a reverse configuration may be provided in which first electrical connector (362) is coupled to shaft assembly (14) and second electrical connector (368) is coupled to handle assembly (12).

First electrical connector (362) of the present example houses first electrical contacts (346) within a slot-like recess (374) that opens to an upper side of first connector body (364). Second electrical connector (368) includes a tab-like projection (376) that extends downwardly from a lower side of second connector body (370) and supports second electrical contacts (372). Recess (374) is configured to receive projection (376) when shaft assembly (14) is coupled to handle assembly (12), as described below, such that first electrical connector (362) provides a female coupling feature and second electrical connector (368) provides a male coupling feature. Recess (374) and projection (376) are formed with generally rectangular complementary shapes in the present example, but may be formed with various other suitable complementary shapes in other examples. In some examples, projection (376) and/or recess (374) may include a plurality of ribs (not shown) positioned between adjacent electrical contacts (366, 372) to function as electrical insulating barriers.

First electrical connector (362) of the present example further includes a first sealing element in the form of a membrane (378) that covers the upper opening of recess (374) and is configured to be breached by projection (376) of second electrical connector (368). Membrane (378) may include a lateral slit (not shown) that facilitates such breach, in a manner similar to membrane slits (316) described above. Second electrical connector (368) of the present example further includes a second sealing element in the form of a compressible seal (380) that fully surrounds a base portion of projection (376) and abuts a lower surface of second connector body (370). Compressible seal (380) is configured to compress against and thereby sealingly engage the upper surface of first connector body (364) when shaft assembly (14) is coupled to handle assembly (12), as described below. Membrane (378) and compressible seal (380) may each be formed of a respective flexible elastomeric material, such as santoprene for example.

Figure 23A:
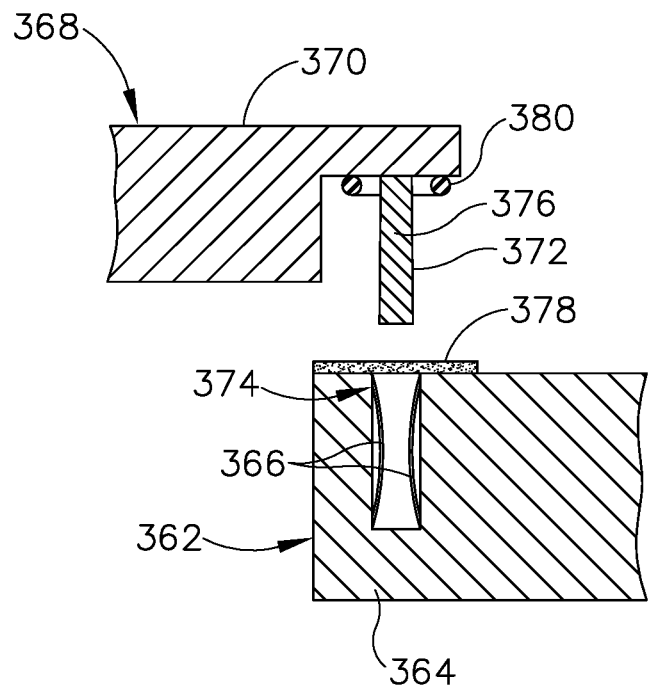
FIG. 23A depicts a side sectional view of the electrical connection assembly of FIG. 22, showing the first and second connectors in a disengaged state.
Figure 23B:
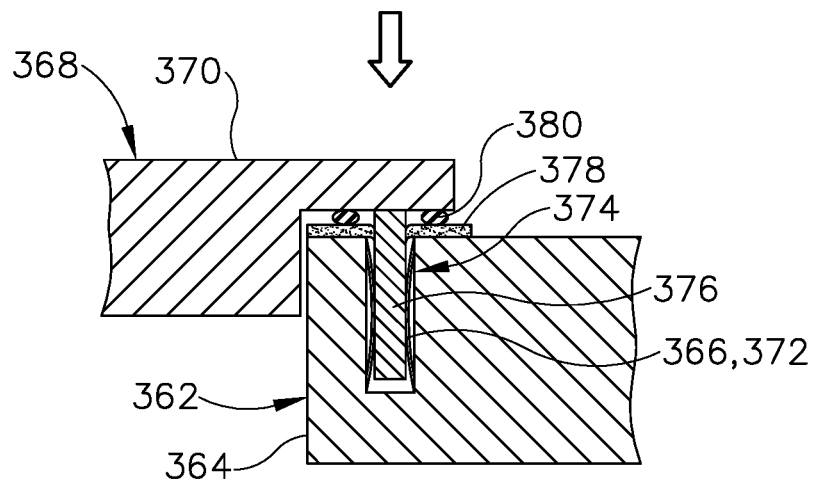
FIG. 23B depicts a side sectional view of the electrical connection assembly of FIG. 23A, showing the first and second connectors in an engaged state.

FIG. 23A shows second electrical connector (368) positioned vertically above first electrical connector (362) as the proximal end of shaft assembly (14) is initially aligned with the distal end of handle assembly (12) along installation axis (IA). As shaft assembly (360) is advanced downwardly along installation axis (IA), projection (376) of second electrical connector (368) breaches downwardly through membrane (378) of first electrical connector (362) and is received within recess (374), as shown in FIG. 23B. This coupling enables first and second electrical contacts (366, 372) to electrically engage and establish an electrical connection. As projection (376) passes downwardly through membrane (378), membrane (378) may wipe any fluid from second electrical contacts (372) to prevent such fluid from entering recess (374).

As projection (376) fully seats within recess (374), compressible seal (380) compresses against and thereby sealingly engages the upper surface of first connector body (364). In this manner, compressible seal (380) establishes a liquid-tight seal that fully surrounds the electrical connection in a plane that extends transversely to installation axis (IA), and further protects the electrical connection from unwanted exposure to fluids that could cause electrical shorting. Advantageously, formation of the liquid-tight seal in a plane transverse to installation axis (IA) eliminates application of shearing forces on compressible seal (380) during engagement of first and second electrical connectors (362, 368).

G. Electrical Connector Having Offset Electrical Contacts

Figure 24:
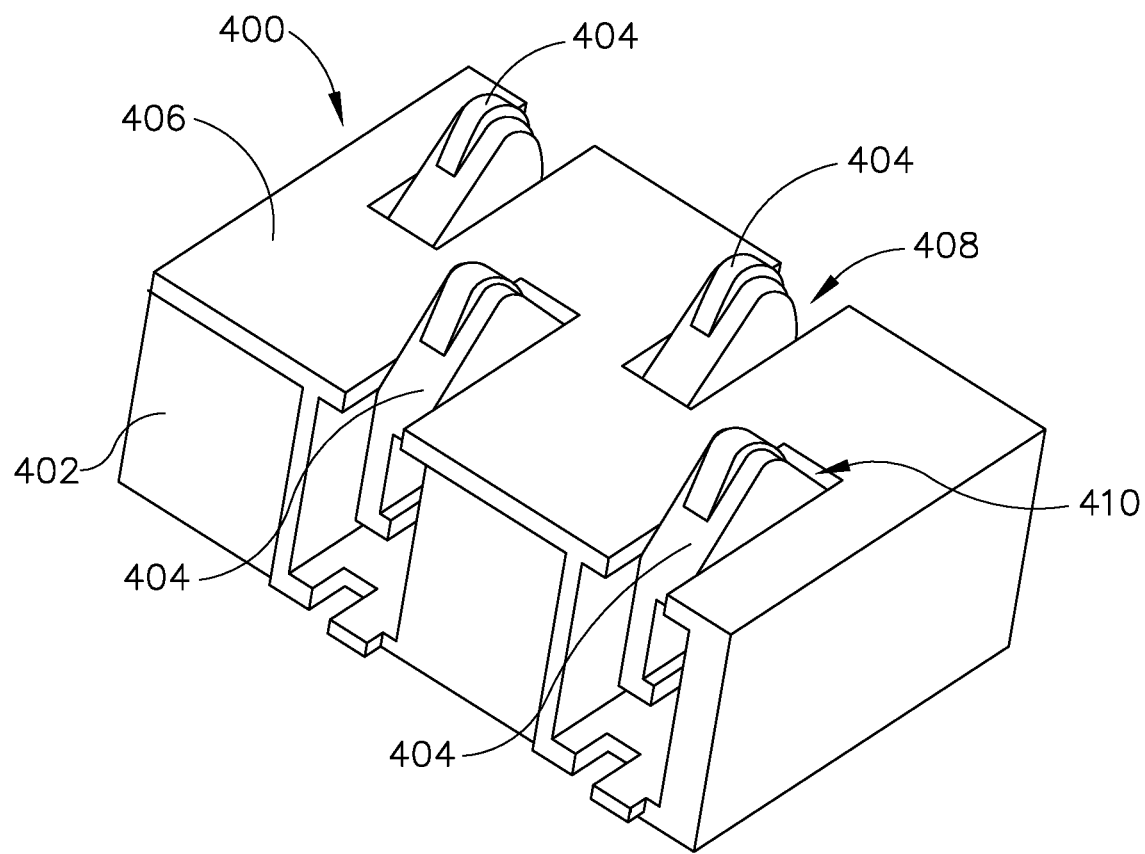
FIG. 24 depicts a perspective view of another exemplary electrical connector suitable for use with the surgical instrument of FIG. 1.

FIG. 24 shows another exemplary electrical connector (400) suitable for use with surgical instrument (10), as well as any of the exemplary electrical connection assemblies (200, 250, 300, 320, 340, 360) described above. Electrical connector (400) includes a connector body (402) and a plurality of electrical contacts (404) supported by connector body (402). Electrical connector (400) is configured to be mounted to handle frame (26) of handle assembly (12), or alternatively to tool chassis (80) of shaft assembly (14), such that electrical contacts (404) extend proximally or distally toward the electrical contacts of a mating electrical connector. Electrical contacts (404) are shown in the form of spring contacts that are configured to resiliently engage the electrical contacts of the opposing electrical connector. Electrical contacts (404) project outwardly from connector body (402) through respective openings formed in an end face (406) thereof.

Electrical contacts (404) of the present example are arranged in a staggered configuration that presents an upper row (408) of electrical contacts (404) and a lower row (410) of electrical contacts (404) that is laterally offset from upper row (408). This staggered configuration promotes electrical isolation of contacts (404), thus reducing the risk of electrical shorting in the presence of fluid. While four electrical contacts (404) are shown in the present example, various other suitable quantities of contacts (404) may be provided in other examples. It will be appreciated that the mating electrical connector configured for use with electrical connector (400) may include a similar staggered configuration of its respective electrical contacts.

Though not shown, electrical connector (400) may further include one or more sealing elements of the exemplary types described above to protect electrical contacts (404) from exposure to fluids during use. For instance, connector (400) may include a membrane similar to any of membranes (280, 314, 334, 378) that covers electrical contacts (404), and/or a compressible seal similar to any of sealing elements (228, 336, 380) that surrounds electrical contacts (404).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body assembly; (b) a shaft assembly, wherein the shaft assembly is configured to releasably attach to and extend distally from the body assembly; (c) an end effector at a distal end of the shaft assembly, wherein the end effector is operable to treat tissue; (d) a first electrical connector coupled to one of the body assembly or the shaft assembly, wherein the first electrical connector includes: (i) a first connector body, and (ii) a first electrical contact recessed within the first connector body; and (e) a second electrical connector coupled to the other of the body assembly or the shaft assembly, wherein the second electrical connector includes: (i) a second connector body, and (ii) a second electrical contact supported by the second connector body, wherein the first connector body is configured to receive the second electrical contact therein to enable the first and second electrical contacts to electrically couple together when the shaft assembly is attached to the body assembly.

Example 2

The surgical instrument of Example 1, wherein the shaft assembly defines a longitudinal axis, wherein the shaft assembly is configured to slide into engagement with the body assembly along an installation axis that extends transversely to the longitudinal axis.

Example 3

The surgical instrument of any of the preceding Examples, further comprising a sealing element supported by one of the first electrical connector or the second electrical connector, wherein the sealing element is configured to block fluid from reaching the first and second electrical contacts when the shaft assembly is attached to the body assembly.

Example 4

The surgical instrument of Example 3, wherein the sealing element comprises a sealing layer, wherein at least one of the first or second electrical contacts is configured to breach the sealing layer when the shaft assembly is attached to the body assembly.

Example 5

The surgical instrument of any of Example 4, wherein the sealing layer comprises a membrane.

Example 6

The surgical instrument of Example 4, wherein the sealing layer includes a duckbill seal.

Example 7

The surgical instrument of any of the preceding Examples, wherein the first and second electrical connectors are configured to sealingly engage one another when the shaft assembly is attached to the body assembly to thereby block fluid from reaching the first and second electrical contacts.

Example 8

The surgical instrument of any of the preceding Examples, wherein the first connector body comprises a compressible body, wherein the compressible body is configured to compress against and thereby sealingly engage the second electrical connector when the shaft assembly is attached to the body assembly.

Example 9

The surgical instrument of any of the preceding Examples, wherein the second electrical contact is configured to project outwardly from the second connector body when the shaft assembly is attached to the body assembly.

Example 10

The surgical instrument of any of the preceding Examples, wherein the second electrical contact is movable relative to the second connector body from a first position to a second position in response to attachment of the shaft assembly to the body assembly, wherein the second electrical contact is configured to electrically couple with the first electrical contact in the second position.

Example 11

The surgical instrument of Example 10, wherein the second electrical contact is movable between the first and second positions in a direction transverse to the installation axis.

Example 12

The surgical instrument of any of the preceding Examples, wherein the second electrical contact comprises a pin, wherein the first electrical contact comprises a spring clip configured to clamp the pin when the shaft assembly is attached to the body assembly.

Example 13

The surgical instrument of any of the preceding Examples, wherein the first electrical connector comprises a female coupling feature that presents the first electrical contact, wherein the second electrical connector comprises a male coupling feature that presents the second electrical contact, wherein the female coupling feature is configured to receive the male coupling feature when the shaft assembly is attached to the body assembly.

Example 14

The surgical instrument of any of the preceding Examples, wherein the first electrical connector includes a plurality of first electrical contacts, wherein the second electrical connector includes a plurality of second electrical contacts, wherein at least one of the plurality of first electrical contacts or the plurality of second electrical contacts is arranged in a staggered configuration.

Example 15

The surgical instrument of any of the preceding Examples, wherein the end effector comprises a stapling assembly operable to drive staples into tissue.

Example 16

A surgical instrument, comprising: (a) a body assembly, wherein the body assembly includes a first electrical contact; (b) a shaft assembly, wherein the shaft assembly is configured to releasably attach to and extend distally from the body assembly, wherein the shaft assembly includes a second electrical contact; (c) an end effector at a distal end of the shaft assembly, wherein the end effector is operable to treat tissue; and (d) a sealing layer supported by one of the body assembly or the shaft assembly, wherein the sealing layer is configured to block fluid from reaching the respective first or second electrical contact when the shaft assembly is disengaged from the body assembly, wherein at least one of the first or second electrical contacts is configured to breach the sealing layer to enable the first and second electrical contacts to electrically couple together when the shaft assembly is attached to the body assembly.

Example 17

The surgical instrument of Example 16, wherein the sealing layer is supported by the body assembly, wherein the second electrical contact is configured to breach the sealing layer when the shaft assembly is attached to the body assembly.

Example 18

The surgical instrument of any of Examples 16 through 17, wherein the body assembly includes a first electrical connector having a first connector body that supports the first electrical contact, wherein the shaft assembly includes a second electrical connector having a second connector body that supports the second electrical contact, wherein the sealing layer is coupled to one of the first connector body or the second connector body.

Example 19

A surgical instrument, comprising: (a) a body assembly; (b) a shaft assembly, wherein the shaft assembly is configured to releasably attach to and extend distally from the body assembly; (c) an end effector at a distal end of the shaft assembly, wherein the end effector is operable to treat tissue; (d) a first electrical connector coupled to one of the body assembly or the shaft assembly, wherein the first electrical connector includes: (i) a connector body, and (ii) a first electrical contact supported by the connector body, wherein the first electrical contact is movable relative to the connector body between a first position and a second position; and (e) a second electrical connector coupled to the other of the body assembly or the shaft assembly, wherein the second electrical connector includes a second electrical contact, wherein the first electrical contact is configured to move from the first position to the second position to thereby electrically couple with the second electrical contact in response to attachment of the shaft assembly to the body assembly.

Example 20

The surgical instrument of Example 19, wherein the second electrical connector includes an engagement feature configured to engage a portion of the first electrical connector and urge the first electrical contact toward the second position when the shaft assembly is attached to the body assembly.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application. Ser. No. 15/934,139, entitled "Surgical Instrument With Compressible Electrical Connector," filed Mar. 23, 2018, issued as U.S. Pat. No. 10,842,517, U.S. application. Ser. No. 15/934,148, entitled "Seal for Surgical Instrument," filed Mar. 23, 2018, issued as U.S. Pat. No. 10,799,257 on Oct. 13, 2020; U.S. application Ser. No. 15/934,166, entitled "Surgical Instrument with Electrical Contact Under Membrane," filed on Mar. 23, 2018, issued as U.S. Pat. No. 10,631,860 on Apr. 28, 2020; U.S. application Ser. No. 15/934,173, entitled "Staple Cartridge with Short Circuit Prevention Features," filed on Mar. 23, 2018, issued as U.S. Pat. No. 10,639,038 on May 5, 2020; U.S. application. Ser. No. 15/934,180, entitled "Surgical Instrument with Capacitive Electrical Interface," filed on Mar. 23, 2018, issued as U.S. Pat. No. 10,779,828 on Sep. 22, 2020; and U.S. application Ser. No. 15/934,190, entitled "Slip Ring Assembly for Surgical Instrument," filed on Mar. 23, 2018, issued as U.S. Pat. No. 10,631,861 on Apr. 22, 2020. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body assembly;
   (b) a shaft assembly, wherein the shaft assembly is configured to releasably attach to and extend distally from the body assembly along a longitudinal axis;
   (c) an end effector at a distal end of the shaft assembly, wherein the end effector is operable to treat tissue;

(d) a first electrical connector coupled to one of the body assembly or the shaft assembly, wherein the first electrical connector includes:
  (i) a first connector body, and
  (ii) a first electrical contact recessed within the first connector body; and
(e) a second electrical connector coupled to the other of the body assembly or the shaft assembly, wherein the second electrical connector includes:
  (i) a second connector body, and
  (ii) a second electrical contact supported by the second connector body,
wherein the first connector body is configured to receive the second electrical contact therein to enable the first and second electrical contacts to electrically couple together when the shaft assembly is attached to the body assembly,
wherein a proximal end of the shaft assembly is configured to slide into engagement with the body assembly along an installation axis that is transverse to the longitudinal axis of the shaft assembly,
wherein one of the first electrical contact or the second electrical contact is movable relative to the respective one of the first connector body or the second connector body to enable the first and second electrical contacts to electrically couple together.

2. The surgical instrument of claim 1, further comprising a sealing element supported by one of the first electrical connector or the second electrical connector, wherein the sealing element is configured to block fluid from reaching the first and second electrical contacts when the shaft assembly is attached to the body assembly.

3. The surgical instrument of claim 2, wherein the sealing element comprises a sealing layer, wherein at least one of the first or second electrical contacts is configured to breach the sealing layer when the shaft assembly is attached to the body assembly.

4. The surgical instrument of claim 3, wherein the sealing layer comprises a membrane.

5. The surgical instrument of claim 3, wherein the sealing layer includes a duckbill seal.

6. The surgical instrument of claim 1, wherein the first and second electrical connectors are configured to sealingly engage one another when the shaft assembly is attached to the body assembly to thereby block fluid from reaching the first and second electrical contacts.

7. The surgical instrument of claim 6, wherein the first connector body comprises a compressible body, wherein the compressible body is configured to compress against and thereby sealingly engage the second electrical connector when the shaft assembly is attached to the body assembly.

8. The surgical instrument of claim 1, wherein the second electrical contact is configured to project outwardly from the second connector body when the shaft assembly is attached to the body assembly.

9. The surgical instrument of claim 1, wherein the second electrical contact is movable relative to the second connector body from a first position to a second position in response to attachment of the shaft assembly to the body assembly, wherein the second electrical contact is configured to electrically couple with the first electrical contact in the second position.

10. The surgical instrument of claim 9, wherein the second electrical contact is movable between the first and second positions in a direction transverse to the installation axis.

11. The surgical instrument of claim 9, wherein the second electrical contact comprises a pin, wherein the first electrical contact comprises a spring clip configured to clamp the pin when the shaft assembly is attached to the body assembly.

12. The surgical instrument of claim 1, wherein the first electrical connector comprises a female coupling feature that presents the first electrical contact, wherein the second electrical connector comprises a male coupling feature that presents the second electrical contact, wherein the female coupling feature is configured to receive the male coupling feature when the shaft assembly is attached to the body assembly.

13. The surgical instrument of claim 1, wherein the first electrical connector includes a plurality of first electrical contacts, wherein the second electrical connector includes a plurality of second electrical contacts, wherein at least one of the plurality of first electrical contacts or the plurality of second electrical contacts is arranged in a staggered configuration.

14. The surgical instrument of claim 1, wherein the end effector comprises a stapling assembly operable to drive staples into tissue.

15. The surgical instrument of claim 1, further comprising a sealing element configured to move from a first position to a second position when the shaft assembly is attached to the body assembly, wherein in the first position the sealing element is recessed within the first connector body, wherein the second position in the sealing element is recessed within the second connector body.

16. The surgical instrument of claim 1, wherein the second electrical contact is movable relative to the second connector body in a direction along the longitudinal axis of the shaft assembly.

17. The surgical instrument of claim 1, wherein the second electrical contact comprises a pin, wherein the first electrical contact comprises a spring clip configured to clamp the pin when the shaft assembly is attached to the body assembly.

18. A surgical instrument, comprising:
(a) a body assembly;
(b) a shaft assembly, wherein the shaft assembly is configured to releasably attach to and extend distally from the body assembly;
(c) an end effector at a distal end of the shaft assembly, wherein the end effector is operable to treat tissue;
(d) a first electrical connector coupled to one of the body assembly or the shaft assembly, wherein the first electrical connector includes:
  (i) a connector body, and
  (ii) a first electrical contact supported by the connector body, wherein the first electrical contact is movable relative to the connector body between a first position and a second position; and
(e) a second electrical connector coupled to the other of the body assembly or the shaft assembly, wherein the second electrical connector includes a second electrical contact,
wherein the first electrical contact is configured to move from the first position to the second position to thereby electrically couple with the second electrical contact in response to attachment of the shaft assembly to the body assembly.

19. The surgical instrument of claim 18, wherein the second electrical connector includes an engagement feature configured to engage a portion of the first electrical connector and urge the first electrical contact toward the second position when the shaft assembly is attached to the body assembly.

20. A surgical instrument, comprising:
(a) a body assembly;
(b) a shaft assembly, wherein the shaft assembly is configured to releasably attach to and extend distally along a longitudinal axis from the body assembly;
(c) an end effector at a distal end of the shaft assembly, wherein the end effector is operable to treat tissue;
(d) a first electrical connector coupled to one of the body assembly or the shaft assembly, wherein the first electrical connector includes:
　(i) a first connector body, and
　(ii) a first electrical contact recessed within the first connector body; and
(e) a second electrical connector coupled to the other of the body assembly or the shaft assembly, wherein the second electrical connector includes:
　(i) a second connector body, and
　(ii) a second electrical contact supported by the second connector body,
wherein the first connector body is configured to receive the second electrical contact therein to enable the first and second electrical contacts to electrically couple together when the shaft assembly is attached to the body assembly,
wherein the second electrical contact is movable relative to the second connector body from a first position to a second position in response to attachment of the shaft assembly to the body assembly, wherein the second electrical contact is configured to electrically couple with the first electrical contact in the second position.

* * * * *